US012029766B2

(12) United States Patent
Gaillard et al.

(10) Patent No.: US 12,029,766 B2
(45) Date of Patent: Jul. 9, 2024

(54) **PHARMACEUTICAL COMPOSITION AND METHODS FOR THE PREVENTION AND/OR TREATMENT OF *STAPHYLOCOCCUS AUREUS* USING ARTIFICIAL BACTERIAL COLONIZATION**

(71) Applicants: UNIVERSITE DE VERSAILLES-ST QUENTIN EN YVELINES, Versailles (FR); ASSISTANCE PUBLIQUE—HOPITAUX DE PARIS, Paris (FR)

(72) Inventors: Jean-Louis Gaillard, Issy les Moulineaux (FR); Didier Guillemot, Paris (FR); Jean-Louis Herrmann, Bourg la Reine (FR); Martin Rottman, La Celle Saint-Cloud (FR); Anne-Sophie Alvarez, Bievres (FR); Jérôme Salomon, Paris (FR); Valérie Lesellier, Igny (FR)

(73) Assignees: UNIVERSITE DE VERSAILLES-ST QUENTIN EN YVELINES, Versailles (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 127 days.

(21) Appl. No.: 16/270,296

(22) Filed: Feb. 7, 2019

(65) Prior Publication Data

US 2019/0167734 A1   Jun. 6, 2019

Related U.S. Application Data

(63) Continuation-in-part of application No. PCT/EP2018/071528, filed on Aug. 8, 2018.

(30) Foreign Application Priority Data

Aug. 8, 2017   (EP) .................................... 17306056

(51) Int. Cl.
| | | |
|---|---|---|
| A61K 35/74 | (2015.01) | |
| A61K 9/00 | (2006.01) | |
| A61K 9/19 | (2006.01) | |
| A61K 35/00 | (2006.01) | |
| A61K 35/66 | (2015.01) | |
| A61P 31/04 | (2006.01) | |
| C12N 1/20 | (2006.01) | |

(52) U.S. Cl.
CPC ............ *A61K 35/74* (2013.01); *A61K 9/0014* (2013.01); *A61K 9/0043* (2013.01); *A61K 9/19* (2013.01); *A61K 35/00* (2013.01); *A61K 35/66* (2013.01); *A61P 31/04* (2018.01); *C12N 1/20* (2013.01)

(58) Field of Classification Search
None
See application file for complete search history.

(56) References Cited

U.S. PATENT DOCUMENTS

2011/0008303 A1\* 1/2011 Liu ...................... A61K 31/351
424/93.42

FOREIGN PATENT DOCUMENTS

WO    2016/172686 A1    10/2016
WO    WO-2016172686 A1 \* 10/2016 ........... A61K 35/741

OTHER PUBLICATIONS

Hong et al., Food Science Biochnology, vol. 23, No. 3, pp. 983-990 (2014)(of record). (Year: 2014).\*
Marteau. "Evidence of probiotic strain specificity makes extrapolation of results impossible from a strain to anther, even from the same species". Annals of Gastroenterology and Hepatology. 2011; 000:(000), www.slm-gastroenterology.com, pp. 1-3.\*
McFarland et al. "Strain-specificity and disease-specificity of probiotic efficacy: a systematic review and meta-analysis". Frontiers in Medicine. May 2018, vol. 8,1 article 124, pp. 1-14.\*
Baur et al., "A Nasal Epithelial Receptor for *Staphylococcus aureus* WTA Governs Adhesion to Epithelial Cells and Modulates Nasal Colonization," 2014. PLoS Pathog, 10(5):e1004089.
Iwase et al., "*Staphylococcus epidermidis* Esp inhibits *Staphylococcus aureus* biofilm formation and nasal colonization," 2010. Nature, 465:346-349.
Kluytmans et al., "Nasal Carriage of Staphylococcus aureus: Epidemiology, Underlying Mechanisms, and Associated Risks," 1997. Clin Microbiol Rev. 10(3):505-20.
Park et al., "Intranasal Application of S. epidermidis Prevents Colonization by Methicillin-Resistant *Staphylococcus aureus* in Mice," 2011. PLoS ONE. 6(10): e25880.
Uehara et al., "Bacterial interference among nasal inhabitants: eradication of *Staphylococcus aureus* from nasal cavities by artificial implantation of *Corynebacterium* sp.," 2000. J Hosp Infect, 44(2): 127-133.
Wertheim et al., "Effect of Mupirocin Treatment on Nasal, Pharyngeal, and Perineal Carriage of *Staphylococcus aureus* in Healthy Adults, " 2005. Antimicrob Agents Chemother, 49(4):1465-1467.
White, "Increased Infection Ratres in Heavy Nasal Carriers of Coagulase-Positive *Staphylococci*," 1963. Antimicrob Agents Chemother, 161: 667-70.
Van Belkum et al., "Reclassification of *Staphylococcus aureus* Nasal Carriage Types," 2009. J Infect Dis. 199: 1820-26.
Yan et al., "Nasal Microenvironments and Interspecific Interactions Influence Nasal Microbiota Complexity and *S. aureus* Carriage," 2013. Cell Host and Microbe, 14(6): 631-640.

(Continued)

*Primary Examiner* — Vera Afremova
(74) *Attorney, Agent, or Firm* — Arrigo, Lee, Guttman & Mouta-Bellum LLP

(57) ABSTRACT

The present invention relates to a pharmaceutical composition comprising at least one *Corynebacterium* sp, *Staphyloccocus pasteuri* and, optionally, *Staphyloccocus epidermidis* for use as a medicament, in particular for use in the prevention or treatment of *S. aureus* colonization.

19 Claims, 6 Drawing Sheets

(56) References Cited

OTHER PUBLICATIONS

Ramsey et al., "*Staphylococcus aureus* Shifts toward Commensalism in Response to *Corynebacterium* Species," 2016. Frontiers in Microbiology, 7:1-15.

Jisoo Hong et al., "A new antimicrobial substance produced by *Staphylococcus pasteuri* isolated from vegetables," 2014. Food science and biotechnology, 23(3): 983-990.

Extended European Search Report, Application No. EP 17306056.7, dated Feb. 5, 2018.

International Search Report, Application No. PCT/EP2018/071528, dated Oct. 22, 2018.

* cited by examiner

A

B

PHARMACEUTICAL COMPOSITION AND METHODS FOR THE PREVENTION AND/OR TREATMENT OF *STAPHYLOCOCCUS AUREUS* USING ARTIFICIAL BACTERIAL COLONIZATION

The present invention relates to the prevention and/or treatment of bacterial colonization by *Staphylococcus aureus*.

The present invention also relates to compositions (e.g. pharmaceutical compositions) comprising at least one *Corynebacterium* sp. and *Staphylococcus* sp. and related methods, said compositions and methods being particularly associated with the prevention and/or treatment of bacterial colonization by *Staphylococcus aureus*.

*Staphylococcus aureus* is a major cause of infection in humans. It is responsible for a wide range of pathologies including skin and soft tissue infections, bone and joint infections, endocarditis, and sepsis. While *S. aureus* can asymptomatically colonize the anterior nares, skin, mucus membranes and gastrointestinal tract, asymptomatic carriage is associated with an increased risk of endogenous *S. aureus* infection, particularly in surgical and dialysis patients. Asymptomatic carriers also act a reservoir for the transmission of *S. aureus*, increasing the risk of infection in both the community and in hospital settings. Indeed, at any given time, an estimated 30% of the population carries *S. aureus* in the anterior nares, the principal site of *S. aureus* colonization.

In order to decrease the risk of transmission and infection by *S. aureus*, in particular in hospital settings where patients are particularly susceptible, many healthcare centers recommend routine patient screening prior to admission, coupled with the elimination of *S. aureus* nasal carriage, otherwise known as "nasal decolonization." Indeed, it has been shown that the risk of infection by *S. aureus* is increased when the level of *S. aureus* present in the nares is high (White, 1963, van Belkum, 2009). Adequate nasal decolonization methods are therefore critical to limiting *S. aureus* transmission and infection.

To date, a variety of methods have been used for nasal decolonization, including the application of local antibiotics and/or antiseptics, the use of systemic antibiotics, and artificial bacterial colonization of the nares. However, local antibiotic and antiseptic treatment methods have low efficacy and have led to the rapid emergence of antiseptic and antibiotic resistance in *S. aureus* strains. The use of systemic antibiotics has similarly led to the rapid emergence of antibiotic resistant strains, coupled with the presence of undesirable side effects. Artificial bacterial colonization consists in the administration of bacterial species and/or strains that compete with *S. aureus*. Notably, artificial colonization of the nares with *S. aureus* strain 502A was used to prevent colonization by more virulent *S. aureus* strains in neonates during outbreaks, and in patients with recurrent infection, in the 1960s. However, this method was abandoned after strain 502A itself was found to be the cause of several *S. aureus* infections and was even linked to a death. More recently, several studies have evaluated the effects of other bacterial species on *S. aureus* colonization in the nares, with varying and often contradictory results. For example, Uehara et al., 2000, has shown that *S. epidermidis* is unable to eliminate *S. aureus* from the nares. In contrast, Iwase et al., 2010, has reported that *S. epidermidis* can in fact eliminate *S. aureus* carriage. Similarly, while Uehara et al., 2000, has shown that artificial colonization with *Corynebacterium* can eliminate *S. aureus* carriage, Yan et al., 2013 has more recently shown that the presence of *Corynebacterium accolens* in the nares is associated with carriage of *S. aureus*. Yan et al., 2013 has further shown that *C. accolens* can facilitate growth of *S. aureus*.

Despite the known disadvantages of local antibiotic administration, nasal decolonization currently relies essentially on the use of a locally applied antibiotic, mupirocin. In efforts to slow the development of *S. aureus* resistance to mupirocin, treatment is limited to patients at risk of severe infection, with antibiotic administration for very short periods of time (e.g. a five-day treatment course in patients undergoing resuscitation or surgery). Attaining patient compliance can be difficult, however, as mupirocin must be applied repeatedly. Furthermore, *S. aureus* recolonization is frequent after treatment, indicating that mupirocin has little long-term treatment effect. Indeed, while mupirocin efficacy is significant, as many as half of the patients remain colonized with the same *S. aureus* strain five weeks after the start of treatment. It has furthermore been reported that mupirocin treatment of individuals exempt from *S. aureus* colonization can be deleterious and cause them to become carriers, making it necessary to screen for carriage prior to treatment (Wertheim et al., 2005).

Despite these efforts, *S. aureus* antibiotic-resistant strains are now detected in up to 50% of patients in rehabilitation and long-term care facilities. Of the antibiotic-resistant strains, methicillin-resistant *S. aureus* (MRSA) is the most prevalent, though cases of mupirocin-resistant MRSA have been reported. Infections due to antibiotic-resistant *S. aureus* (e.g. MRSA) are associated with increased mortality, morbidity, length of hospitalization and cost, when compared to infections due to methicillin-sensitive *S. aureus* (MSSA).

As a result, there exists a need for new products and methods for the prevention and/or treatment of *S. aureus* colonization on the skin and mucus membranes. In particular, there is a need for new products and methods preventing and/or treating *S. aureus* colonization of the nares. There is a further need for new products and methods that can be administered over a long period of time (e.g. weeks or months), in particular for the duration of the healing of an accidental or surgical wound. This need is particularly important in the context of orthopedic and cardiac surgery, in patients bearing implanted devices, and in patients residing in rehabilitation or long-term care facilities, where *S. aureus* colonization and/or infection are frequent. Given the propensity of *S. aureus* to develop antibiotic and antiseptic resistance, these new products and methods should not be based on the use of either antibiotics or antiseptics, and should function in particular in the prevention and/or treatment of MRSA. They should also have few side effects and be available at a reasonable cost.

The present invention is directed to a composition comprising at least one *Corynebacterium* sp. and at least one *Staphylococcus* sp., preferably comprising at least one *Corynebacterium* sp. and at least *S. pasteuri*. The composition according to the invention may comprise any of the preferred characteristics described below relative to the pharmaceutical composition, which is itself a preferred embodiment of the composition. In particular, the composition comprises at least one *Corynebacterium* sp. and *Staphylococcus pasteuri*, wherein said at least one *Corynebacterium* sp. is selected from *C. accolens, C. propinquum, C. pseudodiphtheriticum, C. amycolatum, C. glutamicum, C. aurimucosum, C. tuberculostearicum*, and *C. afermentans*, preferably *C. accolens* and/or *C. propinquum*. Preferably, the composition further comprises *Staphylococcus epidermidis*. Preferably, the composition comprises at least $10^3$ CFUs of *Corynebacterium* sp., at least $10^3$ CFUs of *Staphyloccocus pasteuri*, and, optionally, at least $10^3$ CFUs of *Staphylococcus epidermidis* per dose. Preferably, the composition comprises a total of at least $10^3$ bacterial CFUs per dose, preferably at least $1.2 \times 10^3$, more preferably at least $1.4 \times 10^3$, even more preferably at least $3 \times 10^3$ bacterial CFUs per dose. Preferably, the ratio of *Corynebacterium* sp. to *Staphylococcus pasteuri* to *Staphyloccocus epidermidis* is comprised in the range of 1:0.01:0.01 to 1:1:1. Preferably, the composition further comprises at least one excipient, preferably a pharmaceutically acceptable excipient. Preferably said at least one excipient comprises at least one lyoprotectant, preferably selected from peptone, glycerol, lactose, gelatin, glucose, sucrose, trehalose, dextran, maltodextrin, adonitol, and sodium glutamate. Preferably, the composition is lyophilized or freeze-dried. Preferably, the composition further comprises at least one gelling agent, preferably a pharmaceutically acceptable gelling agent.

Preferably, the present invention is directed to a pharmaceutical composition comprising at least one *Corynebacterium* sp. and at least one *Staphylococcus* sp., preferably comprising at least one *Corynebacterium* sp. and at least *S. pasteuri*. Said at least one *Corynebacterium* sp. is preferably selected from *C. accolens* and *C. propinquum*, or comprises both *C. accolens* and *C. propinquum*. The present invention is further directed to a pharmaceutical composition comprising at least one *Corynebacterium* sp., *S. pasteuri*, and at least one additional *Staphylococcus* sp., preferably *S. epidermidis*. Thus, according to a particularly preferred embodiment, the present invention is further directed to a pharmaceutical composition comprising *C. accolens* and/or *C. propinquum*, *S. pasteuri* and *S. epidermidis*. The invention is further directed to said composition for use as a medicament, in particular in the prevention and/or treatment of *S. aureus* colonization. Indeed, the inventors have surprisingly found that a composition comprising a combination of at least one *Corynebacterium* sp. and *S. pasteuri* or a combination of at least one *Corynebacterium* sp., *S. pasteuri* and *S. epidermidis* can prevent and/or treat *S. aureus* colonization.

The combination of these bacterial species is particularly advantageous as the inventors have surprisingly shown that the three bacterial species *C. accolens*, *S. pasteuri* and *S. epidermidis*, individually inhibit *S. aureus* colonization, with *C. accolens* and *S. pasteuri* having a strong synergistic effect, inhibiting *S. aureus* growth by more than 95%. The inventors have also surprisingly shown that other *Corynebacterium* sp., such as *C. propinquum* similarly inhibit *S. aureus* colonization, with *C. propinquum* and *S. pasteuri* having a particularly strong synergistic effect, inhibiting *S. aureus* growth by more than 98%. Moreover, growth of *C. accolens* is potentiated by *S. pasteuri*, as *C. accolens* does not grow in the absence of *S. pasteuri* in certain conditions. The presence of *S. pasteuri*, or of both *S. pasteuri* and *S. epidermidis*, improves persistence of *Corynebacterium* sp., such as *C. accolens* or *C. propinquum* by enabling the establishment of a biofilm. Furthermore, although a combination of *C. accolens* and *S. epidermidis* has an antagonistic tendency, reducing the inhibitory effect on *S. aureus* growth seen with *S. epidermidis* alone, the combination of all three bacterial species also has surprisingly high anti-*S. aureus* activity, inhibiting *S. aureus* growth by more than 95%. As *S. epidermidis* is an essential colonizer of the nasal flora, it is preferably included in the pharmaceutical combination. *S. epidermidis* may notably provide a protective bacterial layer in vivo, contributing to the prevention of *S. aureus* re-establishment. Thus, a pharmaceutical composition comprising at least one *Corynebacterium* sp., *S. pasteuri* and *S. epidermidis* prevents *S. aureus* colonization, and is particularly advantageous.

The pharmaceutical composition of the present invention is advantageous as the composition is not based on the administration of antibiotics or antiseptics, but rather on the administration of at least two, preferably three bacterial species, thereby minimizing the risk of the emergence of further *S. aureus* resistance. Advantageously, said composition can be administered for longer periods of time than current methods. Advantageously, the present composition can prevent colonization by antibiotic resistant *S. aureus*, such as MRSA, in a patient. Advantageously, the present composition can treat colonization by antibiotic resistant *S. aureus*, such as MRSA, in a patient. The composition of the invention is also advantageous as none of the selected bacterial species possess virulence traits. Even more advantageously, all selected bacterial species are commonly detected in the nasal microflora and/or on the skin of healthy subjects.

Prevention and/or treatment of colonization via the pharmaceutical composition of the present invention is particularly advantageous as colonization is associated with both an increased risk of endogenous infection and transmission. Thus, preventing and/or treating *S. aureus* colonization represents the most effective way of reducing the total number of *S. aureus* infections. Furthermore, current methods for treating *S. aureus* are not recommended for prophylactic use due to the possibility of increasing antibiotic resistance. In contrast, the pharmaceutical composition according to the invention can be administered prophylactically to subjects. The pharmaceutical composition according to the invention can also be administered to subjects colonized by *S. aureus*.

The term "patient" or "subject" is defined herein as any human individual, regardless of their age. In a preferred embodiment, the subject is hospitalized for any reason. In a more preferred embodiment, the subject is hospitalized for cardiac or orthopedic surgery, bears an implanted device, or resides in a rehabilitation or long-term care facility. In cases where the subject is not colonized by *S. aureus* at the time of hospital admission, the pharmaceutical composition of the invention may be used prophylactically, to prevent later colonization by *S. aureus*. Alternatively, in cases where the subject is already colonized by *S. aureus* at the time of hospital admission, the pharmaceutical composition of the invention may be used to treat colonization by *S. aureus*.

The subject may be an adult or child. The term "adult" refers herein to an individual of at least 16 years of age. The term "child" comprises infants from 0-1 years of age and children from 1-8 years of age, 8-12 years of age, and 12-16 years of age. The term "child" further comprises neonatal infants from birth to 28 days of age and post-neonatal infants from 28 to 364 days of age. The composition may be administered to an adult or a child, including neonatal infants. The pharmaceutical composition of the invention is particularly advantageous as existing treatment methods using antibiotics are limited in children due to unwanted side effects.

The pharmaceutically acceptable composition comprises a sufficient quantity of each of the bacterial strains to be therapeutically effective. As a non-limiting example, the pharmaceutical composition may comprise at least $10^2$, $10^3$, $10^4$, $10^5$, $10^6$, $10^7$, $10^8$, $10^9$, $10^{10}$, $10^{11}$, or $10^{12}$ colony forming units (CFUs) of each of the bacterial strains, or a total of at least $10^3$, $10^4$, $10^5$, $10^6$, $10^7$, $10^8$, $10^9$, $10^{10}$, $10^{11}$, or $10^{12}$ CFUs of all bacterial strains taken together. The quantities of each bacterial strain need not be identical. The ratio of the amount of each of the bacterial strains to the other one or more strains is also such that the pharmaceutically acceptable composition is therapeutically effective. As a non-limiting example, when two strains are comprised in the pharmaceutical composition, the ratio of one strain to the other may range from 1:0.01 to 1:2, including for example, ratios of 1:0.02, 1:0.04, 1:0.2, 1:0.4, or 1:1. As a non-limiting example, when three strains are comprised in the pharmaceutical composition, the ratio of one strain to each of the others may range from 1:0.01:0.01 to 1:1:1, including for example, ratios of 1:0.02:0.02, 1:0.1:0.1, or 1:0.2:0.2.

In a preferred embodiment, the pharmaceutical composition of the present invention comprises from $10^3$ to $10^{12}$ CFUs of the at least one *Corynebacterium* sp., from $10^3$ to $10^{12}$ CFUs of *S. pasteuri*, and, optionally, from $10^3$ to $10^{12}$ CFUs of *S. epidermidis* per dose. More preferably, the composition comprises from $10^4$ to $10^{10}$ CFUs of the at least one *Corynebacterium* sp., from $10^4$ to $10^{10}$ CFUs *S. pasteuri* and, optionally, from $10^4$ to $10^{10}$ CFUs of *S. epidermidis* per dose. Even more preferably, the composition comprises $10^5$ to $10^9$ CFUs of the at least one *Corynebacterium* sp., $10^5$ to $10^9$ CFUs *S. pasteuri* and, optionally, from $10^5$ to $10^9$ CFUs of *S. epidermidis* per dose.

Preferably, the composition of the present invention comprises a total bacterial concentration of at least $10^3$, $10^4$, $10^5$, $10^6$, $10^7$, $10^8$, $10^9$, $10^{10}$, $10^{11}$, or $10^{12}$ CFUs, preferably at least 1.2, 1.4, 2 or $3\times10^3$ CFUs, at least 5, 5.02, 5.04, 5.2, or $5.4\times10^3$ CFUs, at least 1.02, 1.04, 1.2, 1.4, 1.5, 2 or $3\times10^4$ CFUs, at least 5, 5.02, 5.04, 5.2, or $5.4\times10^4$ CFUs, at least 1.02, 1.04, 1.2, 1.4, 1.5, 2, or $3\times10^5$ CFUs, at least 1.02, 1.04, 1.2, 1.4, 2, or $3\times10^6$ CFUs, at least 1.02, 1.04, 1.2, 1.4, 2, or $3\times10^7$ CFUs, at least 1.02, 1.04, 1.2, 1.4, 2, or $3\times10^8$ CFUs, at least 1.02, 1.04, 1.2, 1.4, 2 or $3\times10^9$ CFUs, at least $10^{10}$ CFUs, at least 1.02, 1.04, 1.2, 1.4, 2 or $3\times10^{10}$ CFUs, at least 1.02, 1.04, 1.2, 1.4, 2 or $3\times10^{11}$ CFUs, or at least 1.02, 1.04, 1.2, 1.4, 2 or $3\times10^{12}$ CFUs per dose.

The term "dose" is defined herein as amount of the pharmaceutical composition that is administered at a given time. Preferably, the dose administered is therapeutically effective.

The dose may be expressed herein in terms of weight, volume, or CFUs of the pharmaceutical composition.

The term "colony forming unit" or "CFU" is defined herein as a unit used to indicate the number of viable bacteria in a sample, wherein one colony forming unit corresponds to one viable bacterial cell.

In the pharmaceutical composition of the present invention, the ratio in CFUs of the at least one *Corynebacterium* sp. to the at least one *Staphyloccocus* sp. (e.g. the ratio of the at least one *Corynebacterium* sp., preferably *C. accolens*:*S. pasteuri*) is preferably comprised in the range from 1:0.01 to 1:2, more preferably 1:0.01 to 1:1. In the pharmaceutical composition of the present invention, the ratio in CFUs of the at least one *Corynebacterium* sp. to *S. pasteuri* to *S. epidermidis* is preferably comprised in the range from 1:0.01:0.01 to 1:1:1. Advantageously, the ratio of the at least one *Corynebacterium* sp., preferably *C. accolens*, to *S. pasteuri* to *S. epidermidis* is comprised in the range from 1:0.02:0.02 to 1:1:1, preferably from 1:0.1:0.1 to 1:1:1, even more preferably from 1:0.2:0.2 to 1:1:1.

As a non-limiting example, the at least one *Corynebacterium* sp. may be selected from *C. accolens*, *C. propinquum*, *C. pseudodiphtheriticum*, *C. amycolatum*, *C. glutamicum*, *C. aurimucosum*, *C. tuberculostearicum*, or *C. afermentans* in the pharmaceutical composition. The above-mentioned species have notably all been isolated from the nares and/or the skin. The similar effects of different *Corynebacterium* spp. are notably illustrated in the examples. In some cases, two or more *Corynebacterium* spp. may be present in the pharmaceutical composition. For example, *C. accolens* may be combined with at least one other *Corynebacterium* sp., for example selected from one or more of those listed above, such as *C. propinquum*.

According to a preferred embodiment, the at least one *Corynebacterium* sp. is selected from *C. accolens*, *C. propinquum*, *C. pseudodiphtheriticum*, *C. amycolatum*, *C. glutamicum*, *C. aurimucosum*, *C. tuberculostearicum*, and *C. afermentans*. According to a more preferred embodiment, the at least one *Corynebacterium* sp. comprises *C. accolens* or *C. propinquum*, or a combination of both *C. accolens* and *C. propinquum*, according to any of the embodiments described herein. The similar effects of different *C. accolens* strains are notably illustrated in the examples.

In the context of the pharmaceutical composition, any strain of *S. epidermidis* may be used. As a non-limiting example, a strain of *S. epidermidis* may be selected from the strains isolated from the nares.

In the context of the pharmaceutical composition, any strain of the *S. pasteuri* species may be used. The similar effects of different *S. pasteuri* strains are notably illustrated in the examples.

The pharmaceutical composition may be administered prophylactically, in the absence of detection of *S. aureus*, preferably to the skin and/or nares, more preferably to the anterior nares. Alternatively, the pharmaceutical composition may be administered following detection and elimination of *S. aureus* on the skin or in the nares. Alternatively, the pharmaceutical composition may be administered in the absence of testing.

The composition may be administered to a subject one or more times daily (e.g. one, two, three, or four times) and can be administered for several consecutive days (e.g. for one, two, three, four, five, six, seven, eight, nine, ten days or more), weeks (e.g. for one, two, three, four, five, six, seven, eight, nine, ten weeks or more), or months (e.g. for one, two, three, four, five, six months or more). In a preferred embodiment, the composition is administered 1 to 3 times per day for 8 to 12 days, preferably in subjects hospitalized for cardiac or orthopedic surgery. In an alternative preferred embodiment, the composition is administered for weeks or months in subjects bearing an implanted device or residing in a rehabilitation or long-term care facility, or for the duration of the healing of an accidental or surgical wound. In a particularly preferred embodiment, the composition is administered 1 to 3 times per day for one to four weeks, or for one to six months, in subjects bearing an implanted device, residing in a rehabilitation or long-term care facility, or healing from an accidental or surgical wound. In an even more preferred embodiment, the composition is administered for the duration of a hospital stay, the duration of the presence of an implanted device, the duration of residence in a rehabilitation or long-term care facility, or for the duration of the healing of an accidental or surgical wound, preferably 1 to 3 times per day.

Alternatively, the composition may be administered to a subject intermittently (e.g. every other day, every two days, or as necessary) or cyclically (e.g. administration for several days in a row, followed by an absence of administration, or "withdrawal," for several days, at the end of which the cycle is repeated). Preferably, the composition is administered for at least 1 day followed by a period of withdrawal for at least 1 day, followed by the administration for at least 1 day (for example 1 day, 2 days, 3 days, etc.). preferably, this cycle is reproduced several times. Preferably, the composition is administered 1 to 3 times per day. More preferably, the composition is administered for 1 to 12 days followed by a period of withdrawal for 1 to 12 days, followed by the administration for 1 to 12 days. In a preferred embodiment, the composition is administered for 8-12 days followed by a period of withdrawal.

Alternatively, the composition may be administered on demand.

If a protective effect is observed following administration, administration may be repeated as appropriate to maintain said protective effect. If S. aureus colonization is detected following administration of the composition, the administration regimen should be repeated.

The duration and frequency of administration of the composition can be adapted by the skilled person, based on their general knowledge. In particular, the adaptation of these parameters can depend on the length of time during which it is desired that S. aureus colonization is reduced or is absent in the nares and/or on the skin of a subject. For example, it may be desired that S. aureus colonization is absent for the duration of a hospitalization.

In a preferred embodiment of the invention, the pharmaceutical composition further comprises at least one pharmaceutically acceptable excipient.

The term "pharmaceutically acceptable excipient" is defined herein as a component, or combination of components, that is compatible with the pharmaceutical composition, does not generate unwanted side-effects in the patient, and that is generally considered to be non-toxic. A pharmaceutically acceptable excipient is most commonly implicated in facilitating administration of the composition, increasing product shelf-life or efficacy, or improving the solubility or stability of the composition. The pharmaceutically acceptable excipient is generally considered to be pharmacologically inactive. However, in some cases, the excipient itself may also have a therapeutic effect, for example, by making it more difficult for S. aureus to colonize the treated site (i.e. site of administration).

Pharmaceutically acceptable excipients or carriers are well-known in the prior art and can easily be adapted by the skilled person based on the desired galenic formulation of the composition. The galenic formulation, method of administration, and dosage can further be determined based on widely-accepted criteria for adapting patient treatments, including their general health, age, weight, tolerance to treatment, etc., as necessary.

The pharmaceutical composition of the present invention may be administered topically to the epithelium (e.g. the skin) and/or mucus membranes. Preferably, the pharmaceutical composition of the present invention may be administered to the nares, sinuses, or on the axilla, groin, inguinal and perirectal regions, or elsewhere on the skin or mucus membranes. According to a preferred embodiment, the composition is administered to the nares.

The term "nares" as defined herein comprises both the anterior nares or nostrils and the nasal cavity. Preferably, the pharmaceutical composition of the invention is administered to the anterior nares, or nostrils.

While S. aureus may colonize various sites on the human body, it is recognized that its primary ecological niche is the anterior nares, from which it can spread to other tissues or organs (Kluytmans et al., 1997). Much like the skin (e.g. forearm skin), the anterior nares are lined by skin-like, fully keratinized, squamous epithelium with hairs, sebaceous glands and sweat glands. Genetic studies have moreover demonstrated that microbial communities from these two physically distinct niches share identical compositional patterns (Yan et al., 2013). Thus, S. aureus colonization is similar in the skin and anterior nares, with the skin furthermore representing an excellent and easily accessible model for both of these sites.

Advantageously, the composition of the present invention comprises any suitable pharmaceutical preparation for administration to the skin and/or mucus membranes, such as a patch, gel, cream, lotion, ointment, film, emulsion, or salve. Advantageously, the viscosity or texture of the composition is modulated to improve application or efficacy (e.g. contact time). Advantageously, the composition is such that it does not cause adverse effects to the nasal epithelium. Even more advantageously, the pH and/or the osmolarity of the composition is similar to that of the nares.

As the pH of the nasal epithelium is generally within the range of 5.5 to 7.5, the pharmaceutical composition of the present invention advantageously has a pH in said range.

The one or more pharmaceutically acceptable excipients included in the composition of the present invention may further comprise one or more antioxidants, buffers, bulking substances, suspending agents, solubilizing agents, lyoprotectants, matrix forming additives, film formers, humectants, diluents, solvents, plasticizers, oily/emulsifying/aqueous bases, gelling agents, preservatives, tonicity adjusting agents, vehicles, and stabilizers.

As a non-limiting example, the composition of the present invention may comprise at least one pharmaceutically acceptable excipient or carrier well known to the skilled person. Said at least one excipient may be selected from water, glycerin, mineral oils (e.g. vaseline, paraffin), animal oils or fats (e.g. beeswax or wool fat), semi-solid hydrocarbons (oleaginous), or vegetable oils (e.g. coconut oil, mango butter, palm oil, soybean oil, olive oil, shea butter and cacao butter, essential oil), glyceride, xanthan gum, lactose, dextran, mannitol, methylcellulose, hydroxypropyl methylcellulose, hydroxypropyl cellulose, hydroxyethyl cellulose, sodium carboxy methylcellulose, carboxypropyl methylcellulose, polyethelyne glycol, polypropylene glycol, hyaluronic acid, starch-based biodegradeable polymers, tragacanth, pectin, chitin and chitosan derivatives, carrageenan, guar gum, agar, alginate, gelatin, fibrin, albumin, phosphate buffered saline, Polycarbophil, hydrogenated palm oil, glyceride, Carbomer 934P, macrogol, methyl paraben, glyceryl polymethacrylate, cyanoacrylate, triethanolamine, sorbic acid, NaOH, Carbopols (e.g. Carbopol 974P), diazolidinyl urea, Poloxamer 184, dimethicone, cellulose gum, lactic acid, methyl paraben, propylparaben, polyvinyl pyrrolidone, polyvinyl pyrrolidone-vinyl acetate, polyvinyl alcohol, polyacrylic acid, polyacrylamide, homo- and copolymers of acrylic acid crosslinked with a polyalkenyl polyether, sodium hydroxide, sodium chloride, and potassium chloride, and the like.

In a preferred embodiment, the pharmaceutically acceptable composition is a gel, preferably a bioadhesive or mucoadhesive gel. The term "gel" is defined herein as a dispersion of particles interpenetrated with a liquid to generate a semisolid material. The term "bioadhesive gel" is defined herein as a gel which adheres to a biological surface (e.g. stratified squamous epithelium such as the skin or anterior nares). The term "mucoadhesive gel" is defined herein as a gel which adheres to a mucus coat (e.g. mucus membrane).

In a preferred embodiment, the at least one pharmaceutically acceptable excipient is a gelling agent selected from hydroxypropyl methylcellulose, hydroxyethyl cellulose, chitosan and derivatives thereof, for example chitin, carrageenan and derivatives thereof, alginate and derivatives thereof, pectin and derivatives thereof, homo- and copolymers of acrylic acid crosslinked with a polyalkenyl polyether, or mixtures thereof.

If a tonicity adjusting agent is present, said tonicity adjusting agent is preferably selected from potassium chloride, mannitol, dextrose, glycerin, or sodium chloride.

In a preferred embodiment, the pharmaceutical composition comprises at least one gelling agent and at least one tonicity adjusting agent. In a preferred embodiment, sodium chloride is present in the pharmaceutical composition at an isotonic concentration.

If a vehicle is present, said vehicle is preferably selected from water, a water miscible solvent (e.g. glycerin) or a water immiscible solvent (e.g. vegetable oil).

If a preservative is present, said preservative is preferably selected from benzyl alcohol, cresols, benzoic acid, phenol, parabens and sorbic acid.

If a stabilizer is present, said stabilizer is preferably selected from surfactants, polymers, polyols, a poloxamer, albumin, gelatin, trehalose, proteins, sugars, polyvinylpyrrolidone, N-acetyl-tryptophan ("NAT")), caprylate (i.e. sodium caprylate), a polysorbate (i.e. P80), amino acids, and divalent metal cations such as zinc.

According to a further aspect of the invention, bacteria are lyophilized or freeze-dried. "Lyophilization" is a process well known to the skilled person for the removal of water from frozen bacterial cultures by sublimation under reduced pressure. General methods are described in "Lyophilization: Introduction and Basic Principles" (Jennings, 1999). Said process includes the following steps: providing an aqueous formulation comprising viable bacteria, freezing, primary drying (sublimation), and secondary drying (desorption). Lyophilized bacteria are obtained from said process.

According to a preferred mode, bacteria are lyophilized in the presence of a lyoprotectant. The lyoprotectant may be intracellular or extracellular or a combination of both. Preferably, said lyoprotectant is selected from peptone, glycerol, lactose, gelatin, glucose, sucrose, trehalose, dextran, maltodextrin, adonitol, and sodium glutamate.

According to a preferred mode, bacteria are lyophilized in presence of a matrix forming additive. Preferably, said matrix forming additive is mannitol or skim milk.

Preferably, lyophilized bacteria are stored at refrigeration temperatures (e.g. +3 to +6° C.) or at room temperature (e.g. between 20 and 25° C.).

Preferably, each bacterial species is lyophilized separately. According to a first preferred embodiment, each lyophilized bacterial species is reconstituted separately with at least one pharmaceutically acceptable excipient just before use. Reconstituted bacteria may then be administered individually or admixed prior to administration. According to a second preferred embodiment, all bacterial species are admixed together following lyophilization. In this preferred embodiment, lyophilized bacteria are reconstituted together with at least one pharmaceutically acceptable excipient just before use. According to a third preferred embodiment, all bacterial species are admixed together prior to lyophilization. In this preferred embodiment, the mixture is reconstituted with at least one pharmaceutically acceptable excipient just before use.

The "reconstitution" of the lyophilized bacterial composition is defined herein as placing the composition in contact with a specific amount of at least one pharmaceutically acceptable excipient (e.g. a liquid or gel), said excipient hydrating the lyophilizate. Preferably, the mixture is agitated or stirred to ensure complete hydration. Preferably, reconstitution is performed within the range of 17° C. to 37° C., more preferably at or above room temperature (20° C. to 25° C.), even more preferably at room temperature.

Preferably, the composition is reconstituted immediately before use. If the reconstituted composition is not administered immediately, the reconstituted composition is preferably refrigerated until administration. If the reconstituted composition is not administered immediately and is not refrigerated, the reconstituted composition is preferably administered the same day as reconstitution. The skilled person can easily select appropriate reconstitution and storage conditions according to his general knowledge.

According to a first preferred embodiment, separately reconstituted bacteria are administered separately, one after the other. According to a second preferred embodiment, separately reconstituted bacteria are admixed prior to administration for simultaneous application. According to a third preferred embodiment, bacteria that are reconstituted together are administered simultaneously.

Alternatively, viable bacteria may be stored at temperatures comprised between about +4° C. and +8° C. (e.g. for several days), at temperatures comprised between about −25° C. and −40° C. (e.g. for several weeks), or at temperatures comprised between about −72° C. and −85° C. (e.g. for several years). Lyophilized bacteria may also be stored at temperatures comprised between +4° C. and +8° C. for several days following reconstitution. Appropriate storage conditions at each of these temperature ranges are well-known to the person skilled in the art.

The present invention further comprises the pharmaceutical composition for use in the prevention and/or treatment of *S. aureus* colonization. Said pharmaceutical composition for use in the prevention and/or treatment of *S. aureus* colonization comprises all aspects of the pharmaceutical composition of the invention as described herein. Preferably, the invention comprises the pharmaceutical composition for use in the prevention and/or treatment of nasal colonization by *S. aureus*, more preferably, comprising the administration of the composition to the anterior nares, and/or for use in the prevention and/or treatment of skin colonization by *S. aureus*. Skin colonization by *S. aureus* is advantageously prevented and/or treated in a subject having increased susceptibility to said colonization, for example in a subject having an eczema, such as atopic dermatitis, or having diabetes mellitus.

In a preferred embodiment, the invention comprises the pharmaceutical composition for use in the prevention and/or treatment of colonization by antibiotic-resistant *S. aureus*, preferably for use in the prevention and/or treatment of colonization by methicillin-resistant *S. aureus*. More preferably, the pharmaceutical composition is used in the prevention and/or treatment of nasal colonization by methicillin-resistant *S. aureus*. The term "methicillin-resistant" indicates the lack of susceptibility of a bacterial strain to the bactericidal effects of methicillin. MRSA strains may comprise resistance to additional antibiotics (e.g. penicillin, vancomycin, mupirocin, quinolones, etc.). Alternatively, the pharmaceutical composition of the invention may be used in the prevention and/or treatment of nasal colonization by methicillin-sensitive *S. aureus*. Methicillin-sensitive strains are susceptible to the bactericidal effects of methicillin but may comprise resistance to other antibiotics.

The term "colonization by *S. aureus*" is defined herein as the presence of at least one strain of *S. aureus* on a body surface, but that does not induce a detectable immune response and/or that does not invade tissue or otherwise cause tissue damage. Alternatively, colonization may be considered to be the presence of *S. aureus* in the absence of infection. Colonization may be temporary, intermittent, long-term or even permanent in some cases. In particular, colonization by *S. aureus* may occur in the nares, sinuses, throat, gastrointestinal tract, or on the axilla, groin, inguinal and perirectal regions, on wounds, or elsewhere on the skin or mucus membranes. *S. aureus* colonization is a risk factor for later *S. aureus* infection.

The term "infection by *S. aureus*" is defined herein as the presence of at least one strain of *S. aureus* on a body surface inducing a detectable immune response and/or undergoing uncontrolled bacterial growth. The immune response may be specific or non-specific (e.g. fever). *S. aureus* infection can cause skin and soft tissue infections (SSTIs), such as abscesses, furuncles, carbuncles, boils, impetigo, bacterial focculitis or cellulitis, stys, rash, staphylococcal scalded skin syndrome, necrotizing fasciitis, pneumonia, wound infection, endocarditis, gangrene, osteomyelitis, septic arthritis, septicemia, etc.

The term "nasal colonization by *S. aureus*" is more specifically defined herein as the presence of *S. aureus* bacteria in the nares.

The term "nasal decolonization" is defined herein as a method for reducing or eradicating *S. aureus* from the nares. Complete decolonization is defined herein as the absence of detection of *S. aureus* in the nares for at least two consecutive weeks. Partial decolonization is defined herein by the reduction of *S. aureus* in the nares by at least 50% for at least two consecutive weeks as compared to the level of *S. aureus* in the nares prior, preferably by at least 80%, more preferably by at least 90%, more preferably by at least 95%, and even more preferably by at least 99%.

The presence of *S. aureus* bacteria in the nares can be detected by methods well-known in the art, comprising obtaining a sample from the anterior nares, for example via a nasal swab, and detecting *S. aureus*. *S. aureus* can be detected at the species and/or strain level. Detection methods include, for example, culture-based methods (e.g. sample plating on selective media, such as chromogenic and/or blood agar) and molecular diagnostic methods (e.g. PCR, real-time PCR, ribotyping, pulsed-field gel electrophoresis, random amplified polymorphic DNA sequencing, BOX-A1R-based repetitive extragenic palindromic-PCR (BOX-PCR), multilocus sequence typing, whole genome sequencing, etc.).

According to another aspect, the present invention comprises a method of preventing and/or treating *S. aureus* colonization in a human subject in need thereof, comprising administering a therapeutically effective dose of the pharmaceutical composition according to the invention. All aspects of the pharmaceutical composition as described herein are comprised in the method of preventing and/or treating *S. aureus* colonization.

The term "preventing" as used herein are not meant be an exclusively absolute term. Indeed, the term "prevention" as used herein may be a delay in colonization by *S. aureus*, a reduction in the level of colonizing *S. aureus*, or a reduction in the frequency of *S. aureus* colonization.

The terms "treating" or "treatment" and the like as used herein refer more particularly to a reduction in the level of *S. aureus* colonization at the treated site. Said reduction in the level of colonizing *S. aureus* may be partial or complete.

The term "therapeutically effective dose" as used herein refers to an amount of the pharmaceutical composition that is sufficient for preventing and/or treating *S. aureus* colonization at least partially, preferably completely, at the treated site. In the context of prevention and/or treatment of *S. aureus* colonization, this term notably refers to an amount sufficient to delay *S. aureus* colonization or to reduce the level or frequency of *S. aureus* colonization. The therapeutically effective dose may be administered in one or more administrations. In some cases, the pharmaceutical composition may be used to prevent and/or treat *S. aureus* colonization at multiple sites within a single subject (e.g. to both the skin and the anterior nares). In this case, a therapeutically effective dose is administered to each site, and according to the appropriate schema of administration.

Accordingly, the present invention encompasses the use of the pharmaceutical composition for preventing and/or treating colonization by *S. aureus* based on the modalities described herein.

According to a first aspect, the method of preventing and/or treating *S. aureus* colonization comprises the administration of the pharmaceutical composition in which the ratio of *Corynebacterium* sp. to *S. pasteuri* is comprised in the range of 1:0.1 to 1:2, or in which the ratio of *Corynebacterium* sp. to *S. pasteuri* to *S. epidermidis* is comprised in the range of 1:0.01:0.01 to 1:1:1. According to a second aspect, the method of preventing and/or treating *S. aureus* colonization comprises the administration of the pharmaceutical composition having at least $10^3$ CFUs of *Corynebacterium* sp., at least $10^3$ CFUs of *S. pasteuri*, and, optionally, at least $10^3$ CFUs of *S. epidermidis* per dose. Preferably, the method of preventing and/or treating *S. aureus* colonization comprises the administration of the pharmaceutical composition having from $10^3$ to $10^{12}$ CFUs of *Corynebacterium* sp., from $10^3$ to $10^{12}$ CFUs of *S. pasteuri*, and, optionally, from $10^3$ to $10^{12}$ CFUs of *S. epidermidis* per dose. According to a preferred aspect, the method of preventing and/or treating *S. aureus* colonization comprises the administration of the pharmaceutical composition comprises a total of at least $10^3$, preferably at least 1.2, 1.4, 2 or $3 \times 10^3$ CFUs per dose. Preferably, said pharmaceutical composition is lyophilized or freeze-dried.

Preferably, the method of preventing and/or treating *S. aureus* colonization comprises the administration of the pharmaceutical composition further comprising at least one pharmaceutically acceptable excipient. According to a first aspect, said at least one pharmaceutically acceptable excipient is a lyoprotectant, preferably selected from peptone, glycerol, lactose, gelatin, glucose, sucrose, trehalose, dextran, maltodextrin, adonitol, and sodium glutamate. According to a second aspect, said at least one pharmaceutically acceptable excipient is a gelling agent. Said at least one pharmaceutically acceptable excipient may be selected from those listed above, or from excipients that are well known in the art.

Preferably, the method of preventing and/or treating *S. aureus* colonization comprises the administration of the pharmaceutical composition to the anterior nares and/or the skin.

Preferably, the method of preventing and/or treating *S. aureus* colonization of the present invention prevents or reduces *S. aureus* nasal colonization. Preferably, the method of preventing and/or treating *S. aureus* colonization of the present invention prevents or reduces MRSA or MSSA nasal or skin colonization.

A further object of the present invention is a method for preventing nasal or skin colonization by *S. aureus* in a subject comprising:

a) determining if *S. aureus* is present in the nares or on the skin; and b) administering the pharmaceutical composition of the invention to said subject if *S. aureus* is not detected.

A further object of the present invention is a method for treating nasal or skin colonization by *S. aureus* in a subject comprising:
   a) determining if *S. aureus* is present in the nares or on the skin; and
   b) administering the pharmaceutical composition of the invention to said subject if *S. aureus* is detected.

A further object of the present invention is the pharmaceutical composition for use in the prevention and/or treatment of *S. aureus*, comprising
   a) determining if *S. aureus* is present in the nares or on the skin and
   b) administering said pharmaceutical composition.

Preferably, said *S. aureus* present in the nares or on the skin according to any of the above aspects is MRSA or MSSA, preferably MRSA.

The present invention also comprises the use of the composition according to the invention for the manufacture of a medicament for the prevention and/or treatment of colonization by *S. aureus*.

The present invention also comprises the use of the composition according to any of the embodiments described herein in the prevention and/or treatment of colonization by *S. aureus*, preferably in the nares and/or on the skin.

The present invention also comprises a method for preventing and/or treating colonization by *S. aureus* in a subject in need thereof, preferably in the nares and/or skin, comprising administering the composition described herein.

The subject of any of the methods provided herein may be any subject previously identified in the context of the use of said composition. In particular, said subject may be a subject hospitalized for cardiac or orthopedic surgery, a subject bearing an implanted device, a subject residing in a rehabilitation or long-term care facility, a subject having an accidental or surgical wound, a subject having an eczema, such as atopic dermatitis, or a subject having diabetes mellitus.

The present invention has for further object a kit comprising the composition, preferably the pharmaceutical composition, described herein, a gel suitable for nasal and/or skin use and, in case of nasal administration, a means for nasal administration. The present invention has for further object a kit comprising the pharmaceutical composition described herein and:
   a gel, a cream, a lotion, an ointment, an emulsion, or a salve, suitable for nasal use and a means for nasal administration, or
   a gel, a cream, a lotion, an ointment, an emulsion, or a salve, suitable for skin use.
Preferably, the kit comprises:
   a) the pharmaceutical composition comprising *C. accolens, S. pasteuri*, and, optionally, *S. epidermidis*, and at least one pharmaceutically acceptable excipient, said composition having a lyophilizate formulation,
   b) at least one pharmaceutically acceptable component,
   c) a means for nasal administration of said composition, and
   d) optionally, a notice of use.

Preferably, the at least one pharmaceutically acceptable component of b) is an aqueous solution for the reconstitution of said lyophilizate or a gelling agent. More preferably, the component of b) comprises both an aqueous solution for the reconstitution and a pharmaceutically acceptable gelling agent.

*Corynebacterium* sp., may preferably be selected from *C. accolens, C. pseudodiphtheriticum, C. amycolatum, C. glutamicum, C. aurimucosum, C. tuberculostearicum, C. afermentans*, and/or *C. propinquum* in the kit. *C. accolens* may notably be combined with at least one other *Corynebacterium* spp., such as *C. propinquum* in the kit. According to a preferred embodiment, *C. accolens* is replaced by *C. propinquum* in the kit.

A means is also provided herein for dispensing the pharmaceutical composition such that it is applied to the epithelium or mucous membranes, preferably to the nares. The term "means" is defined herein as any device for local, topical application. Preferably, the means for dispensing the pharmaceutical composition also mixes the lyophilized bacteria with the at least one pharmaceutically acceptable excipient, when lyophilized bacteria are used.

In cases where the pharmaceutical composition is present as multiple doses in a single means, a specific means for measuring a single dose may be further comprised. As an example, a single dose may be the equivalent of one or two depressions of a dispenser.

Figure 1:
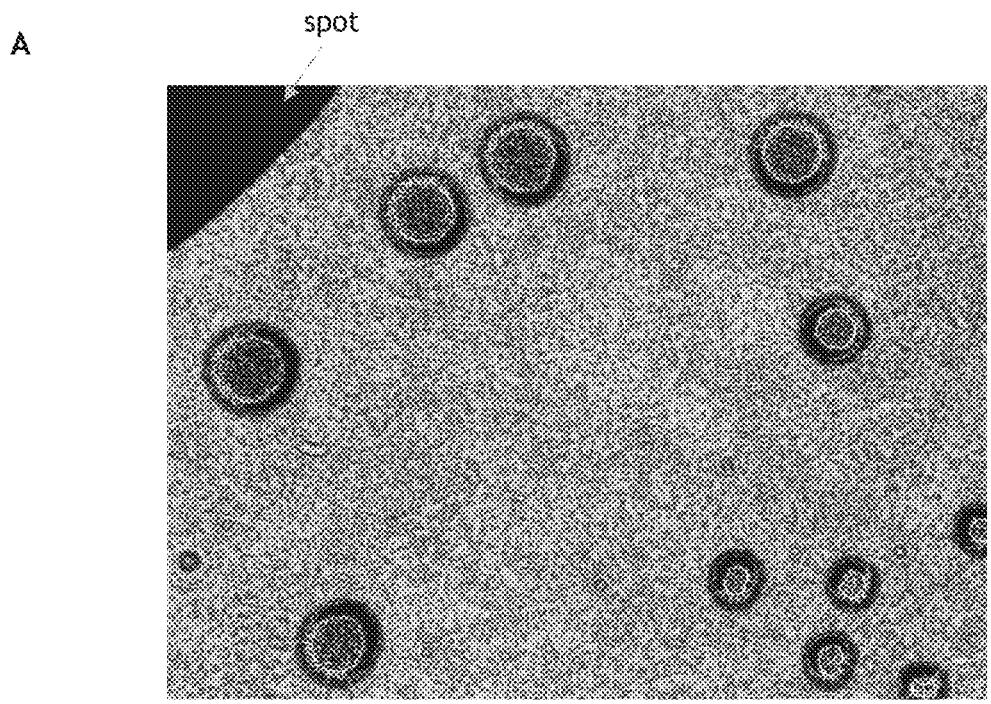
FIG. 1: Growth of *C. accolens* in co-culture with *S. pasteuri* or *S. epidermidis*
Figure 1:
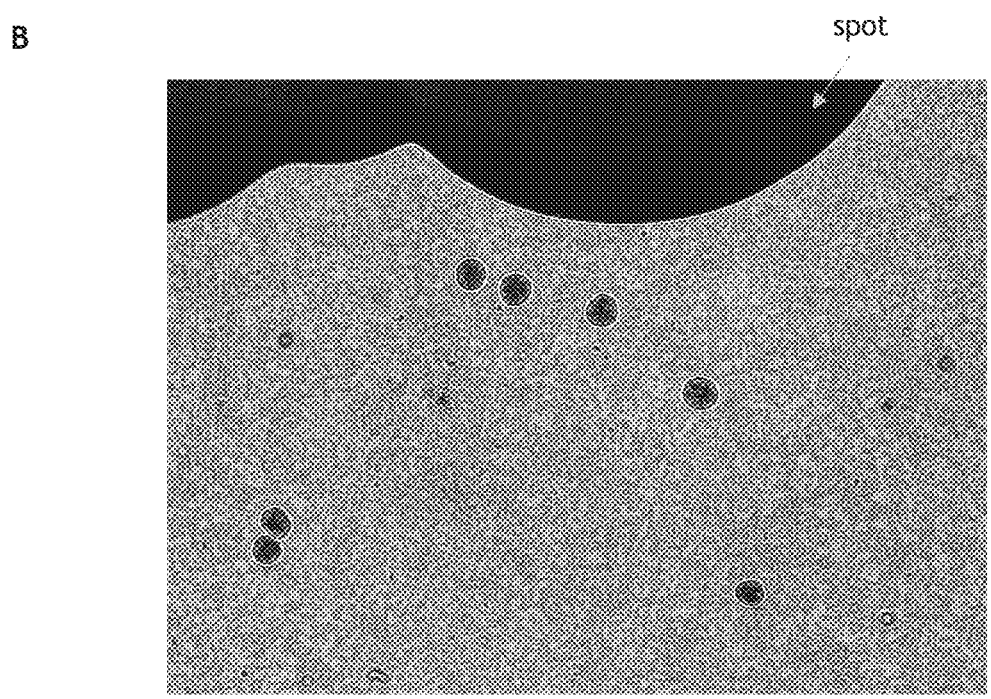

Bacterial growth of *C. accolens* AF2345 was determined in co-culture with either (A) *S. pasteuri* AF2653 or (B) *S. epidermidis* AF2302, according to the methods described in Example 2. *C. accolens* colonies were observed after 72 hours (A) or 7 days (B), at the same magnification. *S. pasteuri* and *S. epidermidis* spots are indicated by an arrow. *C. accolens* colonies are visible in co-culture with *S. pasteuri* with the naked eye, but are smaller with increasing distance from the *S. pasteuri* spot. In contrast, *C. accolens* colonies grown in co-culture with *S. epidermidis* are much smaller than those observed even at a distance from the *S. pasteuri* spot in FIG. 1A, and are not visible with the naked eye.

Figure 2:
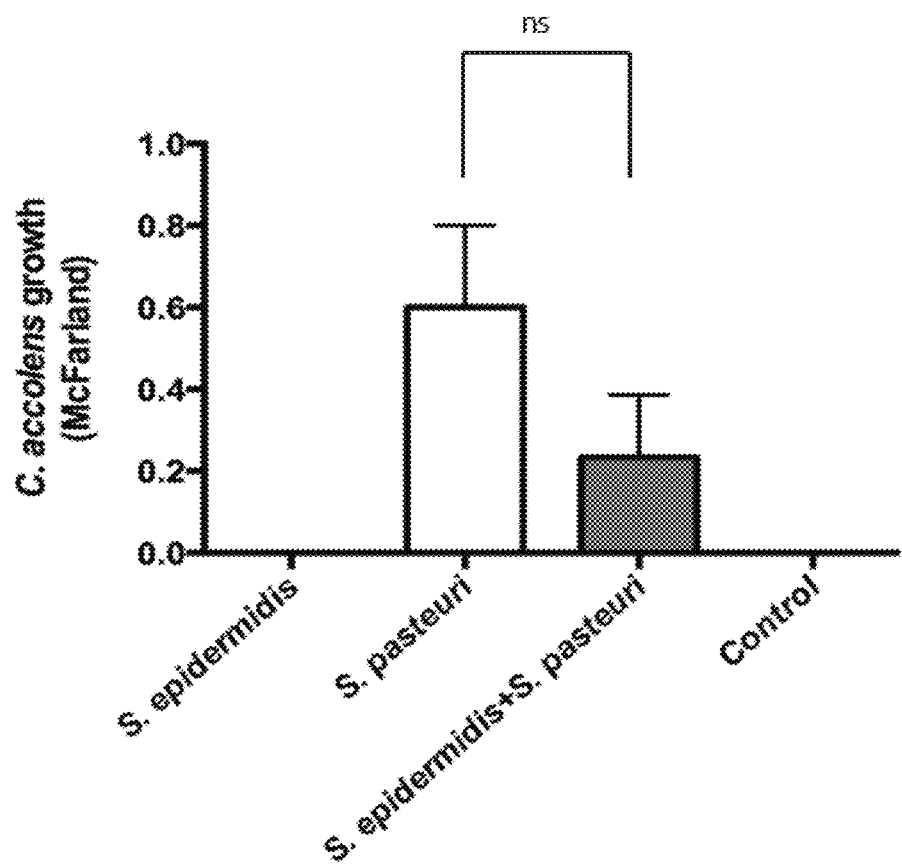

FIG. 2: Mixed biofilms with *C. accolens*

Bacterial growth of *C. accolens* AF2345 alone or as part of a single or mixed biofilm in the presence of *S. pasteuri, S. epidermidis*, or both *S. pasteuri* and *S. epidermidis* was evaluated according to the methods described in Example 8. Growth was observed in the presence of either *S. pasteuri* alone or both *S. pasteuri* and *S. epidermidis*. No significant difference in growth occurred between these two conditions (p=0.0651)

Figure 3:
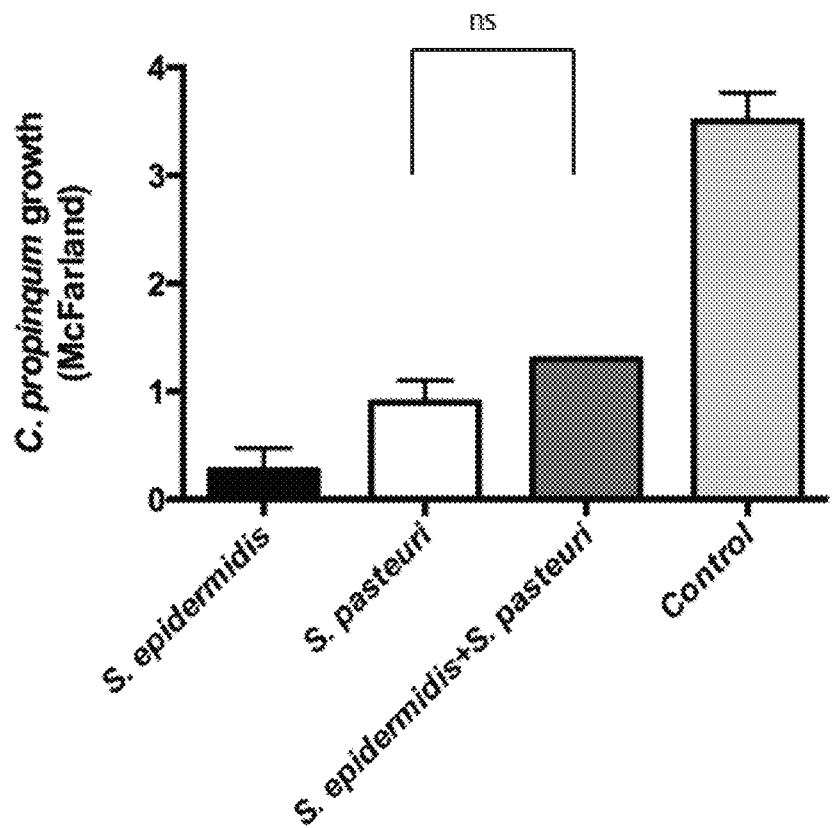

FIG. 3: Mixed biofilms with *C. propinquum*

Bacterial growth of *C. propinquum* AF1882 alone or as part of a single or mixed biofilm in the presence of *S. pasteuri, S. epidermidis*, or both *S. pasteuri* and *S. epidermidis* was evaluated according to the methods described in Examples 8 and 9. Growth was observed in all conditions. No significant difference in growth of *C. propinquum* occurred when in the presence of either *S. pasteuri* alone or both *S. pasteuri* and *S. epidermidis* (p=0.0748).

Figure 4:
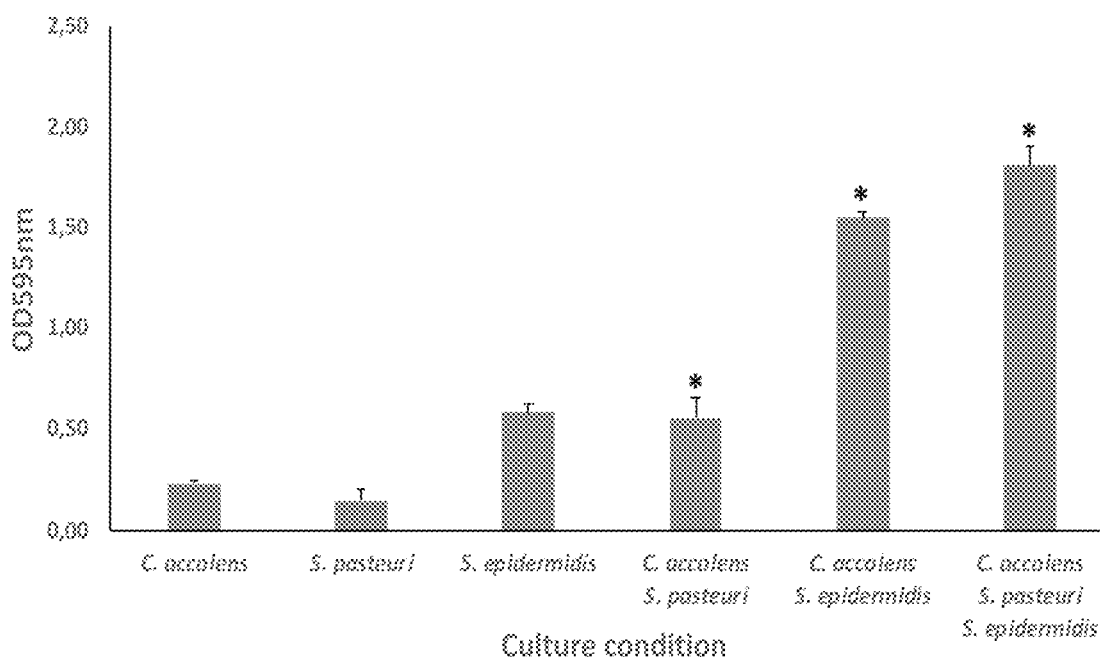

FIG. 4: Production of extracellular matrix when *C. accolens* is co-cultured with *S. pasteuri, S. epidermidis* or both *S. pasteuri* and *S. epidermidis* Bacteria were grown alone or in various combinations in wells of a 96-well plate filled with TSB. Biofilm formation was estimated after 48 hours of incubation at 37° C. by measuring the optical density of solubilized crystal violet-stained extracellular matrix at 595 nm. Production of extracellular matrix was significantly increased when *C. accolens* was co-cultured with *S. pasteuri, S. epidermidis*, or both *S. pasteuri* and *S. epidermidis*.

The greatest effect was obtained with the combination C. accolens/S. pasteuri/S. epidermidis (~7.6-fold increase vs C. accolens alone, 12-fold increase vs S. pasteuri alone and 3.1-fold increase vs S. epidermidis alone).

Figure 5:
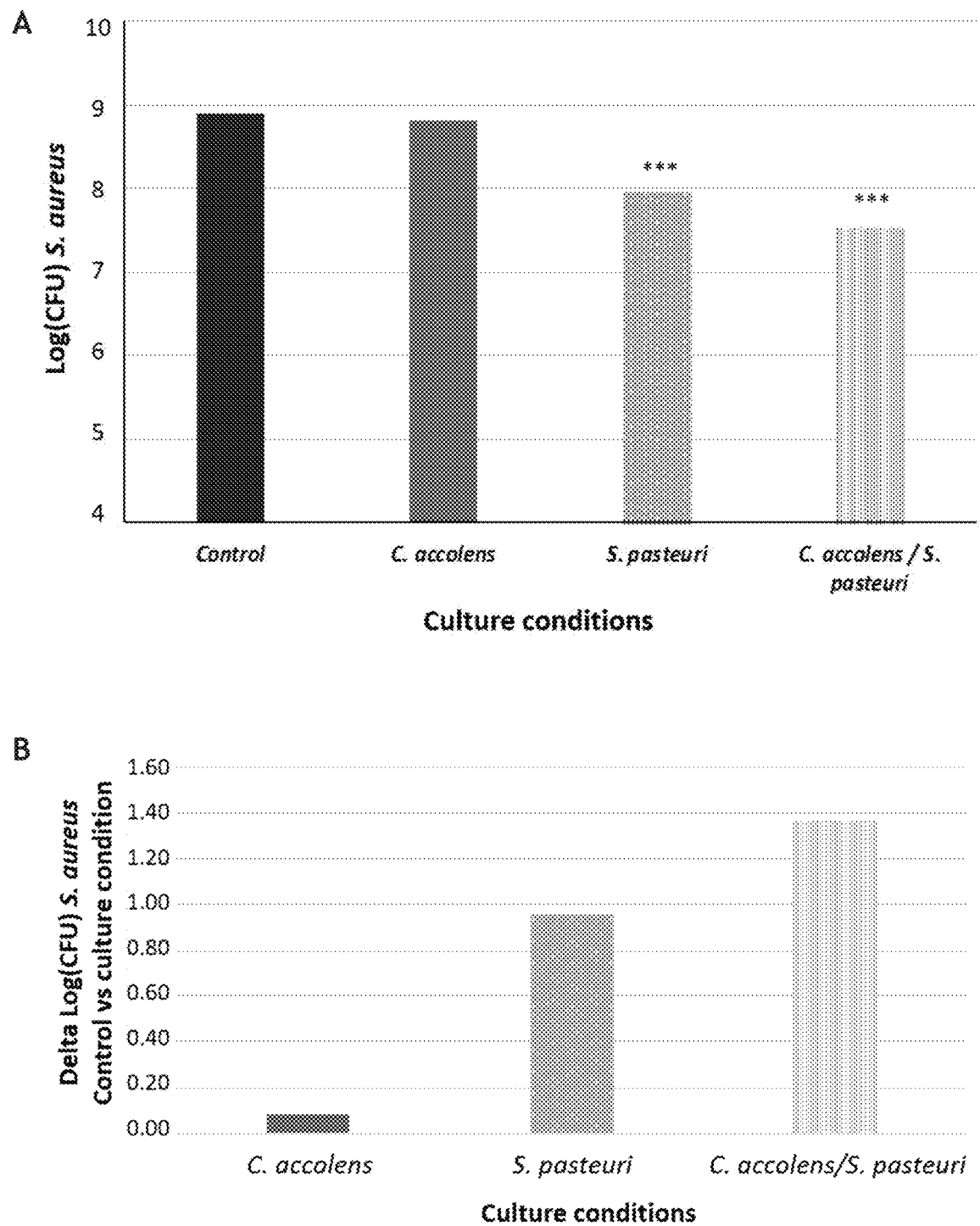

FIG. 5: Bacteriotherapeutic effect of C. accolens/S. pasteuri on adherent S. aureus cells S. aureus bacteria were inoculated in a 96-well plate and were allowed to adhere for 6 h. Bacteria were then treated with C. accolens and/or S. pasteuri ($\approx 5 \times 10^7$ CFU/well for each species). After 24 h of incubation, wells were washed, immersed in an ultrasound bath to disrupt the biofilm, and S. aureus CFUs enumerated. (A) S. aureus $\log_{10}$ CFU. (B) Delta S. aureus $\log_{10}$ CFU (each condition versus control). Although a significant bacteriotherapeutic effect was observed with S. pasteuri alone, the combination C. accolens/S. pasteuri surprisingly showed a further improved synergistic effect. Control: untreated S. aureus cells. **p<0.001 versus control.

Figure 6:
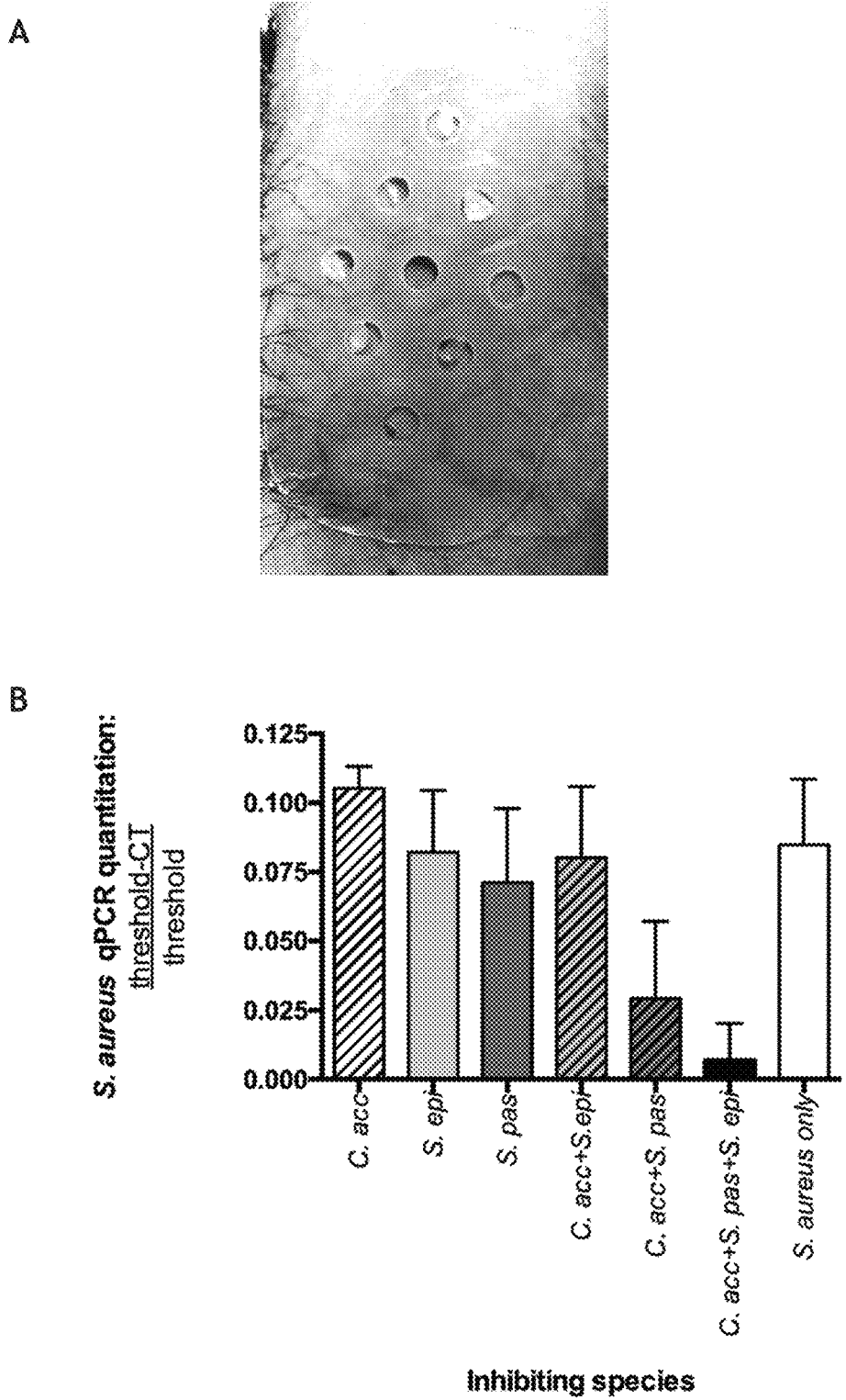

FIG. 6: Prevention of S. aureus colonization in an in vivo model of stratified squamous epithelium (A) Picture of the hydrocolloid patch on a healthy volunteer's forearm skin. Punched holes (corresponding to skin wells) received the bacterial suspensions to be tested covered by the polyurethane sterile incision film. (B) Inhibition of S. aureus 29213 ($5 \times 10^3$ CFU per skin well) when inoculated with C. accolens, S. pasteuri and S. epidermidis alone or combined, each at a dose of $2 \times 10^6$ CFU per well. S. aureus alone was inoculated as positive control. The [(Threshold−CT)/Threshold] ratios are plotted for each condition tested.

Figure 7:
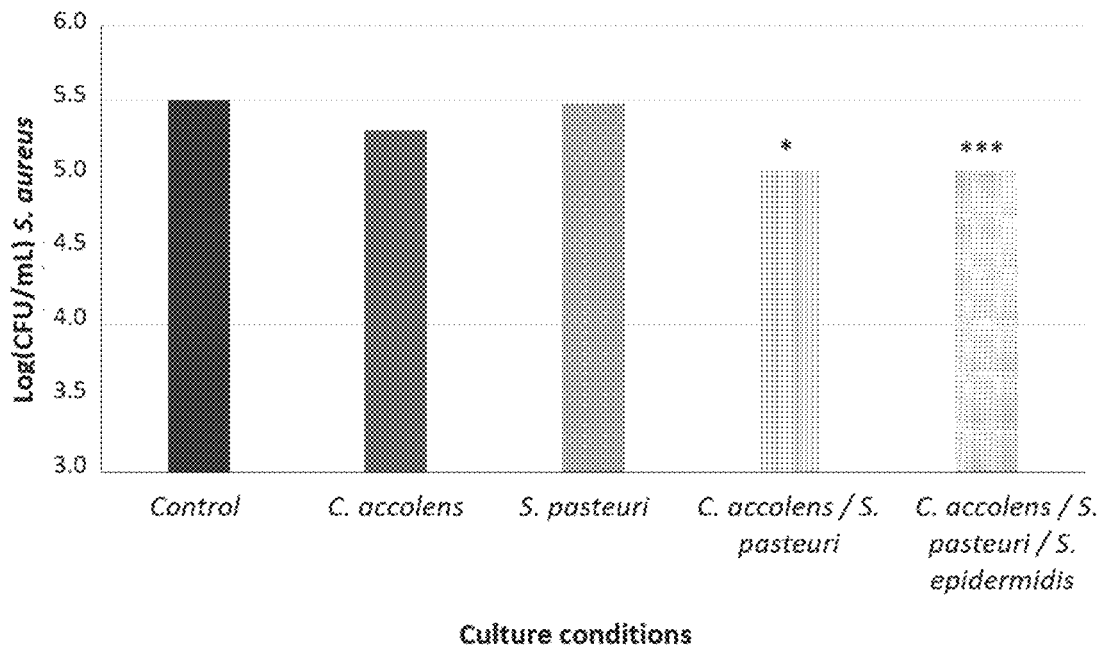
Figure 7:
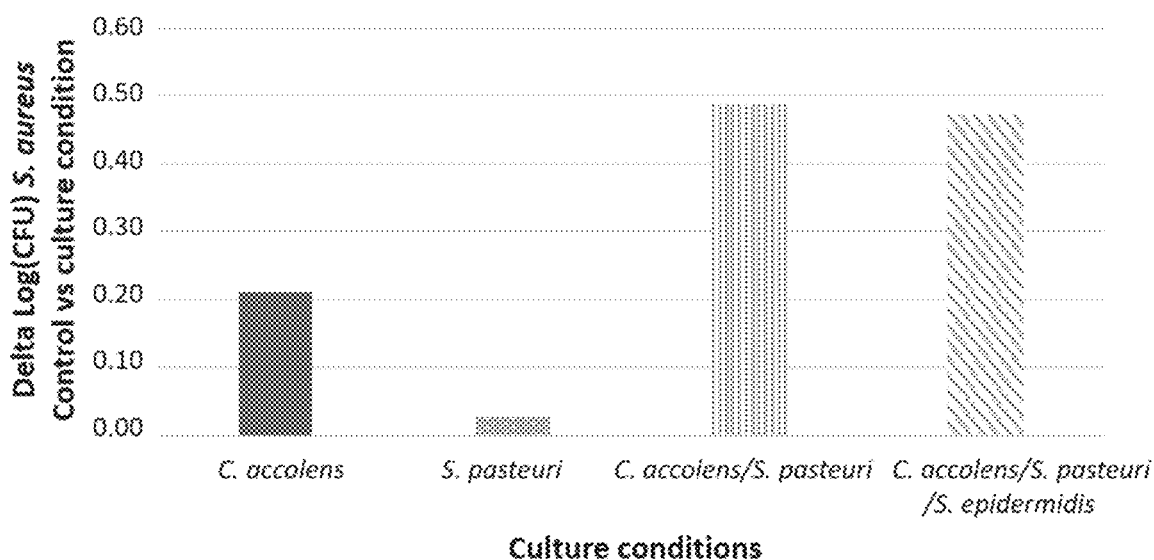

FIG. 7: S. aureus decolonization by bacteriotherapy in an in vivo murine model of stratified squamous epithelium.

Murine stratified squamous epithelium skin wells previously colonized with S. aureus were treated with C. accolens, S. pasteuri and, optionally, S. epidermidis in various combinations, at a dose of $\approx 10^6$ CFU per species. Twenty-four hours later, mice were euthanized, and the area of each skin well was swabbed to quantify S. aureus CFUs. A. S. aureus $\log_{10}$ CFU. B. Delta S. aureus $\log_{10}$ CFU (each condition versus control). A significantly lower level of S. aureus was observed when wells colonized with S. aureus were subjected to bacteriotherapy with the combination C. accolens/S. pasteuri or C. accolens/S. pasteuri/S. epidermidis. The S. aureus burden was 5.50 $\log_{10}$ CFU per well with the control. Control: untreated S. aureus cells. *p<0.05 versus control. **p<0.005 versus control.

EXAMPLES

The following examples are included to demonstrate preferred embodiments of the invention. All subject-matter set forth or shown in the following examples and accompanying drawings is to be interpreted as illustrative and not in a limiting sense. The following examples include any alternatives, equivalents, and modifications that may be determined by a person skilled in the art.

The representative bacterial strains used in these examples are detailed in Table I, below. The strains selected for use in the examples (listed in Table 1) include reference strains, which possess the characteristics representative of all strains of a given species.

TABLE I

Strains used.

| Strain | Source/origin/collection number |
| --- | --- |
| Staphylococcus aureus USA300 ATCC BAA-1556 | MRSA, Wrist abscess |
| Staphylococcus aureus AF3147 | MSSA, nasal swab, our collection |
| Staphylococcus aureus AF2419 | MSSA, nasal swab, our collection |
| Staphylococcus aureus ATCC 29213 | MSSA, S. aureus subsp. aureus Rosenbach (strain Wichita) |
| Corynebacterium accolens AF2345 | Nasal swab, our collection, CNCM I-5395 |
| Corynebacterium accolens AF3612 | Nasal swab, our collection |
| Corynebacterium accolens CIP 104783T | Collection of the Pasteur Institute, Paris, France |
| Corynebacterium propinquum AF1882 | Nasal swab, our collection, CNCM I-5393 |
| Staphylococcus epidermidis AF2302 | Nasal swab, our collection, CNCM I-5394 |
| Staphylococcus pasteuri AF2653 | Nasal swab, our collection, CNCM I-5396 |
| Staphylococcus pasteuri AF2062 | Nasal swab, our collection |
| Staphylococcus pasteuri CIP 103540T | Collection of the Pasteur Institute, Paris, France |
| Staphylococcus pasteuri CIP 103830 | Collection of the Pasteur Institute, Paris, France |

Abbreviations: MRSA, methicillin-resistant Staphylococcus aureus; MSSA, methicillin-susceptible Staphylococcus aureus. Strains with a collection number were deposited with the Collection Nationale de Cultures de Microorganismes (CNCM), Institut Pasteur, 25 rue du Docteur Roux, F75724 Paris CEDEX 15, France on Jan. 25, 2019 by the UFR des sciences de la santé Simone Veil, 2 avenue de la source de la Bievre, 78180 Montigny le Bretonneaux, France, represented by Prof. Jean-Louis Gaillard.

Example 1: In Vitro Inhibition of the Growth of S. aureus by C. accolens

In view of the prior art describing contradictory effects of C. accolens on S. aureus colonization in vivo, the effect of C. accolens on S. aureus growth was first evaluated here in vitro.

Materials and Methods

250 μl of a 1.0 McFarland (McF) suspension of C. accolens, prepared from a 48 h-culture on Columbia 5% sheep blood agar at 35+/−2° C., was inoculated by swabbing on a 90-mm diameter blood agar plate in order to obtain $\approx 5 \times 10^4$ CFU/cm². 250 μl of saline was inoculated as negative control. One 50 mm 0.2 μm track-etched filter was placed on top of the C. accolens suspension. S. aureus suspensions prepared from a 24 h-culture on Columbia −5% sheep blood agar at 35+/−2° C. and containing a target number of 100 CFUs, 10 CFUs, or 1 CFU in 10 µl were spotted on the 50-mm diameter filter.

After incubation for 48 h at 35° C., *S. aureus* colonies on filter were harvested and bacteria resuspended in saline (2.5 to 10 mL). The number of *S. aureus* CFUs present in each colony was then determined by measuring optical density (OD) at 600 nm. To quantify the growth inhibition of *S. aureus* in the presence of *C. accolens*, the OD/colony with or without *C. accolens* was determined. Each set of experiments was repeated at least twice.

Results

*C. accolens* was surprisingly responsible for a reduction of 27.78% to 51.93% of *S. aureus* growth depending on the *C. accolens* and *S. aureus* strain tested (cf. Table II). Also, surprisingly, the growth of both MRSA (*S. aureus* USA300) and MSSA (*S. aureus* AF3147 and AF2419) strains was significantly inhibited. The percent growth inhibition appears to depend on the *C. accolens* strain used, as no significant differences in growth inhibition were observed between different *S. aureus* strains grown in the presence of a same *C. accolens* strain.

detected without magnification. Incubation of *C. accolens* in co-culture with *S. epidermis* for longer periods of time did not further improve *C. accolens* growth, even when the plates were incubated for up to a total of 7 days. Thus, in contrast to *S. epidermidis*, *S. pasteuri* promotes growth of *C. accolens*.

Example 3: Synergistic Inhibition of the Growth of *S. aureus* by *C. accolens* in Combination with *S. pasteuri* In Vitro As *S. pasteuri* promoted *C. accolens* growth, we studied the anti-*S. aureus* activity of *S. pasteuri* and *C. accolens*, alone or in combination. Anti-*S. aureus* activity of *S. epidermidis*, was also tested alone or in combination with *C. accolens*.

Materials and Methods

For each strain alone or in combination, 250 µl of a 1.0 McFarland suspension prepared from cultures on Columbia −5% sheep blood agar at 35+/−2° C. (*C. accolens*: 48 h of incubation; *S. pasteuri, S. epidermidis*: 24 h of incubation) was inoculated by swabbing on a 90 mm diameter blood agar plate (≈5×10$^4$ CFU/cm$^2$). 250 µl of saline was inoculated as negative control. One 50 mm 0.2 µm track-etched filter was placed on top of the spot. *S. aureus* USA300 suspensions containing a target number of 100 CFUs, 10 CFUs, and 1 CFU in 10 µl were spotted on the 50 mm diameter filter. Materials and methods were otherwise as described in Example 1.

TABLE II

| | *S. aureus* growth inhibition (mean (SD), %) | | | | | |
|---|---|---|---|---|---|---|
| *C. accolens* strain | *S. aureus* strain | | | P-value$^a$ USA300 vs AF3147 | P-value$^a$ USA300 vs AF2419 | P-value$^a$ AF3147 vs AF2419 |
| | USA300 | AF3147 | AF2419 | | | |
| AF2345 | 51.75 (2.93) | 51.86 (3.71) | 51.93 (3.33) | 0.969 | 0.946 | 0.980 |
| CIP104783T | 30.01 (3.33) | 27.78 (3.21) | 32.70 (3.33) | 0.437 | 0.361 | 0.115 |
| AF3612 | 41.67 (2.89) | 38.90 (3.21) | 42.32 (3.85) | 0.308 | 0.823 | 0.281 |

$^a$Student's t-test (p values <0.01 were considered as significant),
SD: standard deviation.

Example 2: Growth Promotion of *C. accolens* in Co-Culture with *S. pasteuri*

We next studied the interaction of *C. accolens* and *S. pasteuri* in vitro. The effect of *S. pasteuri* on growth by *C. accolens* was studied using plate count agar (PCA), which allows the growth of *S. pasteuri*, but not that of *C. accolens*. *S. epidermidis* was used as a control species.

Materials and Methods

500 µl of a 10$^{-2}$ dilution of a 0.5 McFarland suspension of *C. accolens* (strain AF2345), prepared as described in Example 1, was inoculated onto PCA medium. After complete drying, 10 µl of a 1.0 McFarland suspension of *S. pasteuri* (strain AF2653) or *S. epidermidis* (strain AF2302), prepared from a 24 h-culture on Columbia −5% sheep blood agar at 35+/−2° C., was spotted at the center of the plate. Ten µl of sterile saline was spotted as a negative control. Growth of *C. accolens* was determined after 72 hours of incubation at 35° C. Growth was determined by the presence of colonies visible with the naked eye.

Results

Growth of *C. accolens* was detected on the periphery of the *S. pasteuri* spot after 72 hours of incubation (FIG. 1A) while abortive colonies were detected around the *S. epidermis* spot (FIG. 1B) or the control spot (not shown). The *C. accolens* colonies detected on the periphery of the *S. pasteuri* spot could be detected with the naked eye, while the abortive colonies around the *S. epidermis* spot could not be Results Table III presents the results obtained with *C. accolens* AF2345, *S. pasteuri* AF2543 and *S. epidermidis* AF2302. As shown, the combination of *C. accolens* and *S. pasteuri* was significantly more inhibitory than each species alone and inhibited *S. aureus* growth by more than 95%. In contrast, the combination of *C. accolens* and *S. epidermidis* was not synergistic and even tended to be antagonistic (mean *S. aureus* growth inhibition of 68.92% versus 79.28% with *S. epidermidis* AF2302 alone, p=0.0133).

TABLE III

| Strain/combination | *S. aureus* growth inhibition (mean (SD), %) | P-value$^a$ |
|---|---|---|
| *C. accolens* AF2345 | 55.96 (2.59) | — |
| *S. pasteuri* AF2653 | 81.87 (2.59) | — |
| *S. epidermidis* AF2302 | 79.28 (3.66) | — |

TABLE III-continued

| Strain/combination | S. aureus growth inhibition (mean (SD), %) | P-value[a] |
|---|---|---|
| C. accolens AF2345 + S. pasteuri AF2653 | 96.12 (1.30) | vs AF2653 alone: $3.4216 \times 10^{-7}$ |
| C. accolens AF2345 + S. epidermidis AF2302 | 68.92 (3.66) | vs AF2302 alone: 0.0133 |

[a]Student's t-test (p values < 0.01 were considered as significant).

We tested other combinations of *C. accolens* and *S. pasteuri* strains in the same conditions. As shown in Table IV, all combinations tested inhibited *S. aureus* inhibition by more than 95%.

TABLE IV

| Combination | S. aureus growth inhibition (%)[a] |
|---|---|
| C. accolens AF2345 + S. pasteuri AF2062 | 99.43 |
| C. accolens AF2345 + S. pasteuri CIP103540T | 95.38 |
| C. accolens AF2345 + S. pasteuri CIP103830 | 99.61 |
| C. accolens CIP104783T + S. pasteuri AF2653 | 95.38 |
| C. accolens CA3612 + S. pasteuri AF2653 | 95.38 |

[a]OD was measured from a pool of ten colonies suspended in saline.

Example 4: Dose-Effect Relationship of the Combination of *C. accolens* and *S. pasteuri*

Materials and Methods

Serial 1/5 dilutions were prepared from a 1.0 McFarland suspension of each strain and 250 µl of each bacterial suspension was inoculated by swabbing on a 90 mm diameter blood agar plate, to obtain each strain alone or in combination at a plated density of $\approx 5 \times 10^4$, $\approx 10^4$, $\approx 2 \times 10^3$, $\approx 4 \times 10^2$, and $\approx 0.8 \times 10^2$ CFU/cm². Materials and methods were otherwise as described in Example 3.

Results

As shown in Table V, the combination of *C. accolens* and *S. pasteuri* was surprisingly significantly synergistic at all bacterial densities tested, with the strongest synergistic effect obtained at $\approx 0.8 \times 10^2$ CFU/cm². However, only the densities superior or equal to $\approx 2 \times 10^3$ CFU/cm² (e.g. $\approx 5 \times 10^4$ CFU/cm², $\approx 10^4$ CFU/cm², and $\approx 2 \times 10^3$ CFU/cm²) showed anti-*S. aureus* activity that inhibited bacterial growth by more than 95%.

TABLE V

| Strain/combination | S. aureus growth inhibition (mean (SD), %) | P-value[a] AF2653 + AF2345 vs AF2653 alone |
|---|---|---|
| $\approx 5 \times 10^4$ CFU/cm² | | |
| C. accolens AF2345 | 50.00 (5.89) | |
| S. pasteuri AF2653 | 86.46 (1.80) | |
| C. accolens AF2345 + S. pasteuri AF2653 | 97.71 (0.36) | $4.1433 \times 10^{-5}$ |
| $\approx 10^4$ CFU/cm² | | |
| C. accolens AF2345 | 41.69 (5.87) | |
| S. pasteuri AF2653 | 80.21 (3.46) | |
| C. accolens AF2345 + S. pasteuri AF2653 | 96.64 (0.47) | 0.0001828 |
| $\approx 2 \times 10^3$ CFU/cm² | | |
| C. accolens AF2345 | 25.02 (5.91) | |
| S. pasteuri AF2653 | 71.88 (3.45) | |
| C. accolens AF2345 + S. pasteuri AF2653 | 95.06 (0.45) | $2.5551 \times 10^{-5}$ |
| $\approx 4 \times 10^2$ CFU/cm² | | |
| C. accolens AF2345 | 14.59 (9.08) | |
| S. pasteuri AF2653 | 54.17 (4.17) | |
| C. accolens AF2345 + S. pasteuri AF2653 | 80.21 (1.81) | $6.0412 \times 10^{-5}$ |
| $\approx 0.8 \times 10^2$ CFU/cm² | | |
| C. accolens AF2345 | 0.00 (0.00) | |
| S. pasteuri AF2653 | 16.66 (5.90) | |
| C. accolens AF2345 + S. pasteuri AF2653 | 73.96 (1.80) | $3.6798 \times 10^{-6}$ |

[a]Student's t-test p values < 0.01 were considered as significant).

Example 5: Anti-*S. aureus* Activity of the Combination of *C. accolens, S. Pasteuri* and *S. epidermidis*

In view of our previous results presented in Example 3, we evaluated whether or not the addition of *S. epidermidis* had a negative impact on the inhibitory activity of the combination of *C. accolens* with *S. pasteuri* against *S. aureus*.

Materials and Methods

For each strain in combination, 250 µl of a 1.0 McFarland suspension prepared from cultures on Columbia −5% sheep blood agar at 35+/−2° C. (*C. accolens:* 48 h of incubation; *S. pasteuri, S. epidermidis:* 24 h of incubation) was inoculated by swabbing on a 90 mm diameter blood agar plate ($\approx 5 \times 10^4$ CFU/cm²); 250 µl of saline was inoculated as negative control. One 50 mm 0.2 µm track-etched filter was placed on top of the spot. A *S. aureus* USA300 suspension containing a target number of 100 CFUs, 10 CFUs, and 1 CFU in 10 µl were spotted on the 50 mm diameter filter. Materials and methods were otherwise as described in Example 1.

Results

As shown on table VI, the same level of *S. aureus* growth inhibition was obtained with the combination *C. accolens* AF2345/*S. pasteuri* AF2653 versus the combination *C. accolens* AF2345/*S. pasteuri* AF2653/*S. epidermidis* AF2302.

TABLE VI

| Combination | S. aureus growth inhibition (mean (SD), %) | P-value[a] AF2345 + AF2653 vs AF2345 + AF2653 + AF2302 |
|---|---|---|
| C. accolens AF2345 + S. pasteuri AF2653 | 98.91 (0.16) | 1.00 |
| C. accolens AF2345 + S. pasteuri AF2653 + S. epidermidis AF2302 | 98.91 (0.16) | |

[a]Student's t-test (p values < 0.01 were considered as significant).

Example 6: *C. propinquum* May Replace *C. accolens* in the Combinations *C. accolens/S. pasteuri* and *C. accolens/S. pasteuri/S. epidermidis*

We then studied whether or not other species of *Corynebacterium*, such as *C. propinquum*, may also have anti-*S. aureus* activity alone and/or in combination with *S. pasteuri* or with *S. pasteuri* and *S. epidermidis*.

Materials and Methods

Materials and methods were as described in Example 3 except that *C. propinquum* AF1882 replaced *C. accolens* AF2345.

Results

As shown in Table VII, the combinations *C. propinquum/S. pasteuri* and *C. propinquum/S. pasteuri/S. epidermidis* were both synergistic and had significant anti-*S. aureus* activity, inhibiting *S. aureus* growth by more than 95%.

TABLE VII

| Strain/combination | *S. aureus* growth inhibition (mean % (SD)) | P-value[a] vs AF1882 alone |
|---|---|---|
| *C. propinquum* AF1882 | 81.25 (4.42) | |
| *C. propinquum* AF1882 + *S. pasteuri* AF2653 | 98.33 (0.30) | 0.002415[b] |
| *C. propinquum* AF1882 + *S. pasteuri* AF2653 + *S. epidermidis* AF2302 | 98.59 (0.27) | 0.0005017[b] |

[a]Student's t-test (p values < 0.01 were considered as significant).
[b]AF1882 + AF2653 versus AF1882 + AF2653 + AF2302, P-value = 0.3524.

Example 7: Anti-*S. aureus* Activity of Bacterial Combinations at Various *Corynebacterium* sp.:*Staphylococcus* sp. ratios The anti-*S. aureus* activity of various ratios of *Corynebacterium* sp.:*Staphylococcus* sp. was also evaluated. In particular, we evaluated various ratios of the combination *C. accolens:S. pasteuri:S. epidermidis* or the combination of *C. propinquum:S. pasteuri:S. epidermidis*.

Materials and Methods

Appropriate dilutions of *C. accolens* AF2345, *C. propinquum* AF1882, *S. pasteuri* AF2653 and *S. epidermidis* AF2302 were prepared from a 2.0 McFarland suspension of each strain and 25 to 250 µl of each bacterial suspension were co-inoculated by swabbing on a 90 mm diameter blood agar plate, thereby obtaining $\approx 10$, $\approx 5 \times 10^4$, $\approx 10^4$, $\approx 5 \times 10$, and $\approx 10^3$ CFU/cm$^2$ of *C. accolens* AF2345 or *C. propinquum* AF1882 combined with *S. pasteuri* AF2653 and *S. epidermidis* AF2302 at the following ratios (*Corynebacterium:S. pasteuri/S. epidermidis*): 1:1:1, 1:0.2:0.2, 1:0.1:0.1, 1:0.02:0.02, 1:0.01:0.01. Materials and methods were otherwise as described in Example 3.

Results

Tables VIII and IX show the results obtained with *C. accolens*- and *C. propinquum*-based combinations, respectively.

As shown in Table VIII, the combination *C. accolens:S. pasteuri:S. epidermidis* surprisingly has an anti-*S. aureus* activity exceeding 95% at all densities and ratios tested, except for ratios 1:0.01:0.01 at densities $\leq 10^4$ CFU/cm$^2$, for ratios 1:0.02:0.02 at densities $\leq 5 \times 10^3$ CFU/cm$^2$, and for ratio 1:0.1:0.1 at a density of $10^3$ CFU/cm$^2$. However, anti-*S. aureus* activities remained significant at all concentrations and densities tested. Indeed, even at the lowest tested concentration and density (e.g. a ratio of 1:0.01:0.01 at a density of $10^3$ CFU/cm$^2$) *S. aureus* growth remained inhibited by at least 74%. Increasing either the ratio (e.g. to 1:0.02:0.02) or the density (e.g. to $5 \times 10^3$) increased anti-*S. aureus* activity, inhibiting *S. aureus* growth by approximately 83% and 85%, respectively.

TABLE VIII

*C. accolens/S. pasteuri/S. epidermidis* combination at various ratios and densities

| Density/ratio | *S. aureus* growth inhibition (mean % (SD)) |
|---|---|
| *C. accolens* at $\approx 10^5$ CFU/cm$^2$ | |
| Ratio[a] 1:1:1 | 99.70 (0.10) |
| Ratio 1:0.2:0.2 | 99.07 (0.19) |
| Ratio 1:0.1:0.1 | 99.27 (0.41) |
| Ratio 1:0.02:0.02 | 97.87 (0.19) |
| Ratio 1:0.01:0.01 | 97.33 (0.19) |
| *C. accolens* at $\approx 5 \times 10^4$ CFU/cm$^2$ | |
| Ratio 1:1:1 | 99.80 (0.00) |
| Ratio 1:0.2:0.2 | 99.33 (0.19) |
| Ratio 1:0.1:0.1 | 98.67 (019) |
| Ratio 1:0.02:0.02 | 97.87 (0.19) |
| Ratio 1:0.01:0.01 | 97.33 (0.38) |
| *C. accolens* at $\approx 10^4$ CFU/cm$^2$ | |
| Ratio 1:1:1 | 99.60 (0.00) |
| Ratio 1:0.2:0.2 | 98.53 (0.19) |
| Ratio 1:0.1:0.1 | 96.40 (1.18) |
| Ratio 1:0.02:0.02 | 96.53 (0.38) |
| Ratio 1:0.01:0.01 | 93.87 (0.38) |
| *C. accolens* at $\approx 5 \times 10^3$ CFU/cm$^2$ | |
| Ratio 1:1:1 | 99.50 (0.10) |
| Ratio 1:0.2:0.2 | 98.53 (0.19) |
| Ratio 1:0.1:0.1 | 96.53 (0.38 |
| Ratio 1:0.02:0.02 | 93.07 (0.38) |
| Ratio 1:0.01:0.01 | 85.07 (0.75) |
| *C. accolens* at $\approx 10^3$ CFU/cm$^2$ | |
| Ratio 1:1:1 | 98.13 (0.19) |
| Ratio 1:0.2:0.2 | 97.73 (0.19) |
| Ratio 1:0.1:0.1 | 92.27 (0.38) |
| Ratio 1:0.02:0.02 | 83.47 (0.75) |
| Ratio 1:0.01:0.01 | 74.93 (0.75) |

[a]Ratio is expressed as the quantity of *C. accolens:S. pasteuri:S. epidermidis*

As shown in Table IX, the results obtained with *C. propinquum* were similar to those obtained with *C. accolens*. Indeed, anti-*S. aureus* activities for bacterial combinations including *C. propinquum* also surprisingly exceeded 95% at all densities and ratios tested, except for ratios 1:0.01:0.01 at densities $\leq 5 \times 10^3$ CFU/cm$^2$, and for ratios 1:0.1:0.1 and 1:0.2:0.2 at a density of $10^3$ CFU/cm$^2$. As seen for combinations with *C. accolens*, anti-*S. aureus* activities of combinations with *C. propinquum* remained significant at all concentrations and densities tested, and were in fact generally higher than those seen for *C. accolens*. Indeed, *S. aureus* growth was inhibited by at least 81% at the lowest tested concentration and density (e.g. a ratio of 1:0.01:0.01 at a density of $10^3$ CFU/cm$^2$). Increasing either the ratio (e.g. to 1:0.02:0.02) or the density (e.g. to $5 \times 10^3$) increased anti-*S. aureus* activity, inhibiting *S. aureus* growth by approximately 89% and 93%, respectively.

TABLE IX

C. propinquum/S. pasteuri/S. epidermidis combination at various ratios and densities

| Density/ratio | S. aureus growth inhibition (mean (SD), %) |
|---|---|
| C. propinquum at ≈$10^5$ CFU/cm$^2$ | |
| Ratio[a] 1:1:1 | 99.80 (0.00) |
| Ratio 1:0.2:0.2 | 99.60 (0.00) |
| Ratio 1:0.1:0.1 | 99.33 (0.19) |
| Ratio 1:0.02:0.02 | 98.13 (0.19) |
| Ratio 1:0.01:0.01 | 97.47 (0.19) |
| C. propinquum at ≈$5 \times 10^4$ CFU/cm$^2$ | |
| Ratio 1:1:1 | 99.50 (0.10) |
| Ratio 1:0.2:0.2 | 99.50 (0.10) |
| Ratio 1:0.1:0.1 | 99.07 (0.19) |
| Ratio 1:0.02:0.02 | 98.67 (0.19) |
| Ratio 1:0.01:0.01 | 97.73 (0.19) |
| C. propinquum at ≈$10^4$ CFU/cm$^2$ | |
| Ratio 1:1:1 | 99.70 (0.10) |
| Ratio 1:0.2:0.2 | 99.50 (0.10) |
| Ratio 1:0.1:0.1 | 98.53 (0.19) |
| Ratio 1:0.02:0.02 | 97.33 (0.19) |
| Ratio 1:0.01:0.01 | 95.87 (0.19) |
| C. propinquum at ≈$5 \times 10^3$ CFU/cm$^2$ | |
| Ratio 1:1:1 | 99.60 (0.00) |
| Ratio 1:0.2:0.2 | 98.93 (0.19) |
| Ratio 1:0.1:0.1 | 97.33 (0.19) |
| Ratio 1:0.02:0.02 | 95.87 (0.19) |
| Ratio 1:0.01:0.01 | 93.73 (0.19) |
| C. propinquum at ≈$10^3$ CFU/cm$^2$ | |
| Ratio 1:1:1 | 98.53 (0.19) |
| Ratio 1:0.2:0.2 | 97.07 (0.19) |
| Ratio 1:0.1:0.1 | 91.73 (0.38) |
| Ratio 1:0.02:0.02 | 89.87 (0.75) |
| Ratio 1:0.01:0.01 | 81.33 (0.75) |

[a]Ratio is expressed as the quantity of C. accolens:S. pasteuri:S. epidermidis

Example 8: C. accolens Forms a Biofilm in the Presence of S. pasteuri

C. accolens requires a complex medium and tryptic soy broth (TSB) does not support its growth. Here we show that C. accolens and S. pasteuri can form a mixed biofilm supporting the growth of C. accolens in conditions where it is normally unable to grow.

Materials and Methods

Bacterial suspensions of a turbidity of McFarland 0.5 were prepared from cultures on Columbia −5% sheep blood agar plates as described in Example 3. 50 μl of the suspension (approx. 2×10 CFU) of C. accolens AF2345 was distributed in 12 wells (row A); 50 μl of a 1:100 dilution (approx. 2×$10^4$ CFU) was distributed in 12 wells (row B); 50 μl of the suspension of S. epidermidis AF2302 (approx. 2×$10^6$ CFU) was distributed in columns 1, 2, 3, 7, 8, and 9; 50 μl of the suspension of S. pasteuri AF2653 (approx. 2×$10^6$ CFU) was distributed in columns 4, 5, 6, 7, 8, and 9. Columns 10, 11, and 12 contain C. accolens AF2345 suspended in 100 μl of culture medium.

The plates were centrifuged, the suspension saline was removed and 100 μl of TSB were added to each well. After 24 hours of incubation, 50 μl of the medium was removed and replaced with fresh TSB. The plates were examined for growth. After 48 hours the plates were observed, the medium removed and the wells gently washed twice with saline. 200 μl of saline was added to each well and the plate immersed in an ultrasound bath to disperse and resuspend the biofilm. For each well, 5 μl (1/40) was transferred to 95 μl of saline (1/800$^{th}$). 5 μl of this suspension was then transferred to a fresh plate containing 95 μl of saline (1/16000$^{th}$). 10 μl of each suspension was then applied to a Mueller Hinton 2 agar plate and to a Mueller Hinton 5% blood NAD enriched defibrinated agar plate containing mupirocin (128 μg/ml).

The bacteria grown after 24 h were suspended in 2.2 ml ampules and the turbidity measured using a McFarland reader.

Results

The results obtained with the high and the low inocula of C. accolens (row A and row B) are qualitatively similar. However, the bacterial density obtained after 24 hours of incubation with the lower inoculum was too low to allow quantification using the McFarland turbidimeter. Data reported hereunder are obtained from the higher inoculum tested (row A).

As expected, C. accolens does not grow in TSB and does not form a biofilm. In contrast, both S. epidermidis and S. pasteuri form a biofilm in TSB (data not shown). Surprisingly, C. accolens is capable of growing within a S. pasteuri biofilm or a mixed S. pasteuri and S. epidermidis biofilm, although it does not grow within a biofilm of S. epidermidis alone (cf. FIG. 2). As expected, no growth is observed in the control wells containing C. accolens in TSB, since it is known that TSB does not support the growth of C. accolens. The difference between the growth of C. accolens in a S. pasteuri biofilm and a S. epidermidis biofilm is significant (p=0.0065). The difference between the growth of C. accolens in a S. pasteuri biofilm and a mixed S. pasteuri and S. epidermidis biofilm does not reach statistical significance (p=0.0651).

Example 9: Growth of C. propinquum in Mixed Biofilms

The same experiment presented in Example 8 was performed by replacing C. accolens with C. propinquum.

Materials and Methods

Experiments were performed as described in Example 8 except that C. propinquum AF1882 were tested instead of C. accolens AF2345.

Results

As shown in FIG. 3, C. propinquum is capable of forming a robust biofilm in TSB. It can also form mixed biofilms in combination with S. epidermidis and S. pasteuri. The growth within S. epidermidis is significantly lower than growth in biofilms containing S. pasteuri (p=0.019). However, as was the case with C. accolens, the presence of S. epidermidis does not adversely affect the growth within C. accolens containing biofilms (C. propinquum with S. pasteuri versus C. propinquum with S. pasteuri and S. epidermidis, p=0.0748).

Example 10: Synergistic Effect of Combining C. accolens with S. pasteuri and/or S. Epidermidis on Biofilm Formation In addition to the quantification of bacterial growth (as illustrated above in Examples 8 and 9), biofilm formation of C. accolens grown alone or in combination with S. pasteuri, S. epidermidis, or both S. pasteuri and S. epidermidis was evaluated here by staining the extra-cellular matrix with crystal violet, which allows the relative quantification of biofilm formation in vitro.

Materials and Methods 1.0 McFarland suspensions of *C. accolens* AF2345, *S. pasteuri* AF2653 and *S. epidermidis* AF2302 were prepared in tryptic soy broth (TSB) as described in Example 1. Fifty µL of the undiluted *C. accolens* suspension and 50 µL of a $10^{-2}$ dilution of the *S. pasteuri* and *S. epidermidis* suspensions were seeded in the wells of a 96-well plate either alone or combined as follows: *C. accolens/S. pasteuri*, *C. accolens/S. epidermidis* and *C. accolens/S. pasteuri/S. epidermidis*. The volume was completed to 200 µL per well with TSB and the plate was incubated at 37° C. After incubation for 48 hours, the wells were rinsed with distilled water, air-dried and the biofilm was stained with 200 µL of a 0.2% crystal violet solution prepared in distilled water. The wells were then rinsed with distilled water, air-dried and the fixed crystal violet solubilized in 200 µL of a 30% acetic acid solution prepared in distilled water. 100 µL of the solubilized crystal violet solution was transferred to a new 96-well plate and the biofilm extra-cellular matrix quantified by measuring the optical density of the suspension at 595 nm.

Results

As shown in FIG. 4, significantly more extracellular matrix was produced when *C. accolens* was grown in combination with *S. pasteuri*, *S. epidermidis* or both *S. pasteuri* and *S. epidermidis* than with each bacterial species alone. Enhancement of extracellular matrix production was the highest with the combination *C. accolens/S. pasteuri/S. epidermidis*.

Furthermore, the quantity of extracellular matrix produced by the combined bacteria was greater than the expected additive effect expected in view of the quantity produced by each species alone. Thus, a synergistic effect is observed when *C. accolens* is co-cultured with *S. pasteuri* and/or *S. epidermidis*. The effect is maximal when *C. accolens* is co-cultured with both *S. pasteuri* and *S. epidermidis*.

Example 11: Treatment of Adherent *S. aureus* Cells with the Combination *C. accolens/S. pasteuri* Inhibits *S. aureus* Development and Biofilm Formation We further studied whether treatment with *C. accolens* alone, *S. pasteuri* alone or the combination *C. accolens/S. pasteuri* had a bacteriotherapeutic effect on *S. aureus*, in particular inhibiting the development and biofilm formation of already adherent *S. aureus*.

Materials and Methods

A 1.0 McF suspension of *S. aureus* (strain USA300) was prepared from a 24 h-culture on Columbia 5% sheep blood agar at 35+/−2° C., in sterile water. 200 µl of this suspension diluted 1:100,000 in Trypto-Casein-Soy (TCS)+5% glucose was inoculated into wells ($\approx 10^3$ CFU/well) of a 96-well plate and incubated for 6 h at 35+/−2° C.

50 McF, 5 McF and 3 McF suspensions of *C. accolens* (strain AF2345) and *S. pasteuri* (strain AF2653), respectively, were prepared in TCS supplemented with 0.05% polysorbate 80 (also referred to as Tween 80 or T80) from a 48 h-culture (*C. accolens*) or a 24 h-culture (*S. pasteuri*) on Columbia 5% sheep blood agar at 35+/−2° C. These suspensions were further diluted in TCS+T80 0.05% in order to obtain a bacterial concentration of $\approx 10^8$ CFU/mL After 6 h of incubation at 35+/−2° C., 100 µl of the *S. aureus* suspension was eliminated per well in the 96-well plate, and replaced by 100 µl of bacterial suspension (*C. accolens* alone, *S. pasteuri* alone, or a combination of *C. accolens/S. pasteuri*), thus at a concentration of $\approx 10^7$ CFU/well for each species. 100 µl of TCS+T80 0.05% also was added in place of the bacterial suspension in control wells ("untreated *S. aureus*").

After further incubation for 24 h at 35+/−2° C., wells were washed three times, filled with 200 µl of sterile water, and immersed in an ultrasound bath to disperse and resuspend the biofilm. *S. aureus* CFUs were enumerated on MRSA agar plates (Biomérieux, Marcy-l'Etoile, France). Results were measured in triplicate and expressed as the mean $\log_{10}$ CFU and as the mean percent of CFU reduction versus control.

Results

As shown in FIG. 5, while both *C. accolens* and *S. pasteuri* alone had a bacteriotherapeutic effect, inhibiting *S. aureus* development and biofilm formation, the combination *C. accolens/S. pasteuri* showed an even stronger bacteriotherapeutic effect. *S. aureus* levels were notably reduced from 8.90 $\log_{10}$ CFU/mL to 7.53 $\log_{10}$ CFU/mL (FIG. 5A), corresponding to a mean CFU reduction of 95.0%.

Surprisingly, the bacteriotherapeutic effect observed with the combination of *C. accolens/S. pasteuri* was synergistic as it was greater than with *C. accolens* alone, *S. pasteuri* alone, or the expected effect of the combination of *C. accolens/S. pasteuri* (FIG. 5B).

Thus, the development of *S. aureus* cells adhering on a surface is the most efficiently combatted by the synergistic combination of at least *C. accolens* and *S. pasteuri*.

Example 12: Treatment of Adherent *S. aureus* Cells with the Combination *C. propinquum/S. pasteuri* Inhibits *S. aureus* Development and Biofilm Formation We further determined if other species of *Corynebacterium*, such as *C. propinquum*, may also inhibit *S. aureus* development and biofilm formation.

Materials and Methods

Materials and methods were as described in Example 11 except that *C. propinquum* AF1882 (bacterial suspension: 2 McF) replaced *C. accolens* AF2345 (bacterial suspension: 50 McF). Reference strain *S. pasteuri* CIP 103830 was used in a similar manner to *S. pasteuri* AF2653 as described in Example 11.

Results

The mean $\log_{10}$ CFU of *S. aureus* was significantly lower when adherent *S. aureus* cells were treated with the combination *C. propinquum/S. pasteuri* (8.45±0.24 versus 9.61±0.12 for untreated *S. aureus* cells, p=0.0008), with a mean CFU reduction of 92.76%. Thus, the combination of *C. propinquum/S. pasteuri* may also inhibit *S. aureus* development and biofilm formation.

Example 13: Reconstituted Lyophilized Bacteria Prevent *S. aureus* Colonization As the final formulation may include freeze-drying the bacteria, we verified that this process does not impair *C. accolens*' ability, in combination with *S. pasteuri* and *S. epidermidis*, to prevent growth of *S. aureus* in vitro. We therefore compared the anti-*S. aureus* activity of "fresh" versus reconstituted freeze-dried bacteria.

Materials and Methods

Bacterial suspensions of *C. accolens* AF2345, *S. pasteuri* AF2652 and *S. epidermidis* AF2302 were combined at a 1:1:1 or a 1:0.1:0.1 ratio, respectively, in freeze-drying buffer. One part of these suspensions, hereafter named "fresh bacteria," was used to inoculate 90 mm petri dishes at final densities of $10^3$ CFU/cm$^2$, $10^2$ CFU/cm$^2$ or $10^1$ CFU/cm$^2$ by swabbing 300 μL of the suspension on the surface of the agar plate. 300 μl of sterile water was inoculated as negative control. One 50 mm 0.2 μm track-etched filter was placed on top of the inoculated surface and *S. aureus* USA300 suspensions containing a target number of 10 and 100 CFU in 10 μl were spotted in triplicate on the filter surface. Materials and methods were otherwise as described in Example 3. The other part of the prepared suspensions was lyophilized in a shelf freeze dryer, using a two-stage process at negative pressure (primary drying: sub-zero temperatures; secondary drying: 15° C.). At the end of the process the vials were sealed under vacuum and stored at 4° C. in the dark until use. On the day of the assay, the lyophilized cake was resuspended in 400 μL of sterile water and the reconstituted suspensions were inoculated according to the same conditions and dilutions as were used for the fresh bacterial suspensions.

Results

As shown below in Table X, the inhibition of *S. aureus* growth is similar when using fresh or reconstituted lyophilized *C. accolens/S. pasteuri/S. epidermidis* combinations, regardless of the bacterial density or ratio tested in the assay (no significant differences are observed).

TABLE X

Anti-*S. aureus* activity of fresh or reconstituted *C. accolens/S. pasteuri/S. epidermidis* combinations at various densities.

| | *S. aureus* growth inhibition, mean % (SD) | | P-value[a] Fresh vs lyophilized bacteria |
|---|---|---|---|
| Density | Fresh bacteria | Lyophilized bacteria | |
| 1:1:1 *C. accolens/S. pasteuri/S. epidermidis* ratio | | | |
| *C. accolens* at ≈$10^3$ CFU/cm$^2$ | 96.82 (0.70) | 96.54 (0.46) | 0.60 |
| *C. accolens* at ≈$10^2$ CFU/cm$^2$ | 90.35 (2.00) | 88.95 (0.56) | 0.31 |
| *C. accolens* at ≈$10^1$ CFU/cm$^2$ | 63.40 (3.08) | 66.12 (3.08) | 0.34 |
| 1:0.1:0.1 *C. accolens/S. pasteuri/S. epidermidis* ratio | | | |
| *C. accolens* at ≈$10^3$ CFU/cm$^2$ | 90.95 (0.65) | 91.11 (0.76) | 0.80 |
| *C. accolens* at ≈$10^2$ CFU/cm$^2$ | 66.77 (3.50) | 61.32 (6.60) | 0.27 |
| *C. accolens* at ≈$10^1$ CFU/cm$^2$ | 23.95 (10.85) | 20.65 (8.04) | 0.69 |

[a]Student's t-test (p < 0.05 for significance).

Thus, freeze-drying a combination of bacteria (in this case *C. accolens, S. pasteuri* and *S. epidermidis*) does not impair the anti-*S. aureus* activity of the bacterial combination. *S. aureus* colonization may therefore still be successfully prevented.

Example 14: The Combination *C. accolens/S. Pasteuri*, and, Optionally, *S. Epidermidis* Inhibits *S. aureus* Nasal Colonization in Mice We studied here the capacity of the combination *C. accolens/S. pasteuri*, and, optionally, *S. epidermidis* to reduce *S. aureus* nasal colonization in the mouse.

Materials and Methods

Six-week old BALB/c_JRj mice were obtained from Janvier Labs (Le Genest-Saint-Isle, France) and were used after one week of acclimatization (IERP, INRA, Jouy-en-Josas, France). A 10 McF suspension of *S. aureus* (strain USA300) in normal saline (≈$10^9$ CFU/mL) was prepared from a 24 h-culture on Columbia 5% sheep blood agar at 35+/−2° C. Lyophilized *C. accolens* (strain AF2345), *S. pasteuri* (strain AF2653) and *S. epidermidis* (strain AF2302) were reconstituted with sterile distilled water in order to obtain a suspension of ≈$2.10^{10}$ CFU/mL for each species. Mice were inoculated intranasally with *S. aureus* (≈$10^7$ CFU) and the combination *C. accolens/S. pasteuri/S. epidermidis* ($0.10^8$ CFU for each species, thus ≈$3\times10^8$ CFU, ratio 1:1:1) at a final volume of 10 μl per nostril; *S. aureus* alone was inoculated as a control ("untreated *S. aureus*"). At 6 h post-inoculation, mice were euthanized and the two nostrils were sampled with a single 0.6 mm interdental brush (GUM; Levallois-Perret; France) to quantify *S. aureus* CFUs as described in example 11. Results were expressed as the mean+/−standard deviation (SD) per animal (five measurements) of the $\log_{10}$ CFU of *S. aureus* and as the mean percentage of *S. aureus* CFU reduction versus control.

Results

The application of the combination *C. accolens/S. pasteuri/S. epidermidis* significantly reduced *S. aureus* nasal colonization (mean (SD): 3.91 (0.46) $\log_{10}$ CFU vs 4.68 (0.64) $\log_{10}$ CFU for control; p=0.030), with a mean CFU reduction of 86.4%.

Thus, the combination *C. accolens/S. pasteuri/S. epidermidis* also shows anti-*S. aureus* activity by the intranasal route.

Example 15: Synergistic Effect of Combining *C. accolens* with *S. pasteuri* and/or *S. epidermidis* in Preventing of *S. aureus* Colonization In Vivo in a Human Skin Model We studied the capacity of freeze-dried strains of *C. accolens, S. pasteuri* and *S. epidermidis* formulated alone or in various combinations to inhibit *S. aureus* growth on the forearm skin of a healthy individual using punched hydrocolloid sterile patches as templates to outline the experimental area (as illustrated in FIG. 6A). Indeed, as indicated previously, the forearm skin is an excellent model of both the skin and anterior nares, in view of the similarities in structure and microbial community composition between these sites.

Materials and Methods

Vials of lyophilized *C. accolens* strain AF2345, *S. pasteuri* strain AF2652 and *S. epidermidis* strain AF2302 were prepared as described in Example 13. Nine evenly spaced 4.5 mm diameter holes were punched in hydrocolloid sterile patches, each hole constituting a 30 μl skin-bottom well. On the day of the assay, two patches were applied to the skin of the internal aspect of the forearm of an informed consenting healthy human volunteer. The lyophilized bacterial cakes were resuspended in sterile water and diluted to a concentration of $3\times10^8$ CFU/mL. *S. aureus* ATCC 29213 was subcultured on blood agar and a saline suspension having a turbidity of 1 McFarland was prepared and diluted to obtain a suspension of ~$10^8$ CFU/mL.

*C. accolens, S. pasteuri* and *S. epidermidis* alone or in various combinations were added to the skin wells at a dose of $2\times10^6$ CFU per species per well and *S. aureus* at a dose of $5\times10^3$ CFU per well. The hydrocolloid patches and the surrounding skin was then covered by sterile polyurethane adhesive surgical incision film (FIG. 6A). The patches were left in place for 30 hours, after which they were peeled off and the skin area corresponding to each well sampled with a humidified swab to quantify *S. aureus*. The head of the swabs were cut using sterile surgical clippers and collected in sterile containers. DNA was extracted using Dneasy Blood and Tissue Kit (Qiagen), according the manufacturer's protocol. DNA extracts were amplified by quantitative real time PCR (qPCR) on the CFX96 C1000 Touch real time system (Biorad) using primers targeting the Spa gene. The reaction mixture was prepared with 1× Itaq Universal Probes supermix (Biorad), 500 nM for each primer, 250 nM probe and DNA template in a final volume of 20 µl. For qPCR, an initial denaturation step (95° C., 5 min) was followed by 40 cycles of 95° C. 15 s and 60° C. for 1 min. Forty amplification cycles were performed and the CT determined. Results were expressed as the [(Threshold−CT)/Threshold] ratio. This ratio reaches one when Spa DNA is detectable without amplification, and reaches zero when there is no detection of Spa DNA at the end of the 40-cycle amplification.
Results FIG. 6B shows the [(Threshold−CT)/Threshold] ratios obtained with *S. aureus* qPCR after co-incubation of *C. accolens*, *S. pasteuri* and *S. epidermidis* alone and in various combinations. When taken alone, none of the species inhibited *S. aureus* growth. In contrast, a synergistic inhibition of *S. aureus* growth was observed for the bacterial combinations *C. accolens/S. pasteuri* (2.9-fold reduction *S. aureus* in growth when compared to growth of *S. aureus* alone) or the combination *C. accolens/S. pasteuri/S. epidermidis* (12.6-fold reduction), in accordance with the present invention.

No irritation, erythema or alteration of the skin of the volunteer was observed.

Example 16: The Combination *C. accolens/S. Pasteuri* Shows a Synergistic *S. aureus* Decolonization Effect in a Murine Model of Stratified Squamous Epithelium Our previous results obtained in vitro showed a synergistic bacteriotherapeutic activity of the combination *C. accolens/S. pasteuri* against *S. aureus* cells in vitro (see Example 11). We studied here the capacity of this combination to reduce *S. aureus* colonization (*S. aureus* decolonization) in an in vivo model of stratified squamous epithelium relevant for both the skin and anterior nares, using Nude mice. We further evaluated whether *S. epidermidis* had an antagonistic effect towards the combination *C. accolens/S. pasteuri*.
Materials and Methods Six-week old BALB/cAnNRj-Fox1 nu/nu mice were obtained from Janvier Labs (Le Genest-Saint-Isle, France) and were used after one week of acclimatization (IERP, INRA, Jouy-en-Josas, France). A 10 McF suspension of *S. aureus* (strain USA300) in physiological water (PSA) was prepared from a 24 h-culture on Columbia 5% sheep blood agar at 35+/−2° C. After homogenization, ≈250 µl was vaporized (Amber boston glass bottle, One Trillion, China) on the back of each mouse. Twenty-four hours later, a hydrocolloid sterile patch (Compeed, Paris, France) having five evenly spaced punched holes (diameter: 4.5 mm) was applied to the back of each mouse, with each hole constituting a 30 µl skin-bottom well. Lyophilized suspension of *C. accolens* (strain AF2345), *S. pasteuri* (strain AF2653) and optionally *S. epidermidis* (strain AF2302) were reconstituted with distilled sterile water to obtain a suspension of ≈$10^{10}$ CFU/mL for each species. Bacteria were inoculated in the skin well at a volume of 10 µl (≈$10^8$ CFU per skin well). The hydrocolloid patch and the surrounding skin were then covered by sterile polyurethane adhesive surgical incision film. Four conditions were tested: *C. accolens* alone; *S. pasteuri* alone; *C. accolens* combined with *S. pasteuri*; *C. accolens* combined *S. pasteuri* and *S. epidermidis*); 10 µl of physiological water was inoculated as control ("untreated *S. aureus*").

Twenty-four hours later, mice were euthanized, the adhesive surgical incision film was peeled, and the skin area of each well was sampled with a humidified swab (ESwab®, COPAN, Brescia, Italy), and *S. aureus* CFUs enumerated by counting CFUs on MRSA agar (Biomérieux, Marcy-l'Etoile, France). Results were measured in duplicate and expressed as the mean+/−SD $\log_{10}$ CFU and as the mean percentage of CFU reduction versus control.
Results Firstly, it should be noted that the mean number of *S. aureus* CFUs found with the control was 5.51 per well area (15.9 mm$^2$). Thus, *S. aureus* skin colonization reached a density of ≈$2 \times 10^4$ CFU/mm$^2$ 48 h post-inoculation, confirming the relevance of our model compared to available models of *S. aureus* nasal colonization in rodents. Indeed, in comparison, in an "optimized" model of nasal colonization using mice treated with oral streptomycin to reduce the natural nasal flora, ≈$5 \times 10^3$ CFUs of *S. aureus*/nose was found 8 hours after the intranasal instillation of $5 \times 10^8$ CFUs of *S. aureus* (Park et al., 2011). Similarly, in the cotton rat model, a well-established model for *S. aureus* nasal colonization which also requires the oral treatment of animals with streptomycin, *S. aureus* colonization was ≈$5 \times 10^4$ CFU/nose 8 hours after inoculation (Baur et al., 2014). As *S. aureus* colonization occurs in the murine model used herein at levels similar to those described existing murine models, this model represents a clinically relevant model that should be considered as an appropriate equivalent to existing models.

The combination *C. accolens/S. pasteuri* showed a significant decolonization effect compared to the control (untreated *S. aureus*), with a mean CFU reduction of 72.6% (p<0.005 versus control); this effect was synergistic as it was greater than with *C. accolens* alone, *S. pasteuri* alone, or the expected effect of the combination of *C. accolens/S. pasteuri* (FIG. 7B).

The combination *C. accolens/S. pasteuri/S. epidermidis* also showed a significant effect, with a comparable CFU reduction (66.5%, p<0.005 versus control). *S. epidermidis* thus had no impact on the decolonization effect of the combination of *C. accolens/S. pasteuri*.

CONCLUSION

Taken together, these Examples illustrate the surprising synergistic anti-*S. aureus* activity that occurs when combining at least one *Corynebacterium* sp., such as *C. accolens* or *C. propinquum*, with *S. pasteuri*, and, optionally, *S. epidermidis*. Furthermore, these results indicate that *S. pasteuri* particularly promotes growth of *Corynebacterium* spp. such as *C. accolens*, and furthermore promotes biofilm formation of *C. accolens* in a synergistic manner when in co-culture as illustrated by quantification of the extracellular matrix. Biofilm formation was similarly improved in a synergistic manner when a *Corynebacterium* sp. was cultured with both *S. pasteuri* and *S. epidermidis*. Advantageously, a composition comprising said bacterial species can furthermore be successfully lyophilized and reconstituted with no loss of effect, as the reconstituted composition prevents *S. aureus* colonization at the same level as fresh bacteria. Bacteriotherapeutic effects were clearly illustrated in murine models of both *S. aureus* nasal colonization and more generally in decolonization of stratified squamous epithelium, which functions as model of both the skin and the anterior nares.

Furthermore, administration of the composition to human forearm skin, which represents the most common ecological niches of *S. aureus* (i.e. the skin and the anterior nares), yielded similar results, greatly reducing colonization by *S. aureus* in vivo.

These Examples provide the first evidence that a composition comprising at least one *Corynebacterium* sp., preferably at least *C. accolens* or *C. propinquum*, and *S. pasteuri*, and, preferably also *S. epidermidis*, represents a novel, unexpected and highly advantageous composition for use in the prevention and/or treatment of both MSSA and MRSA *S. aureus* colonization.

REFERENCES

Baur et al., 2014. *PLoS Pathog*, 10(5):e1004089.
Iwase et al., 2010. *Nature*, 465:346-349.
Jennings, 1999. *Lyophilization: Introduction and Basic Principles*. Interpharm/CRC Press, Denver.
Kluytmans et al., 1997. *Clin Microbiol Rev.* 10(3):505-20.
Park et al., 2011. *PLoS ONE.* 6(10): e25880.
Uehara et al., 2000. *J Hosp Infect*, 44(2): 127-133.
Wertheim et al., 2005. *Antimicrob Agents Chemother*, 49(4): 1465-1467.
White, 1963. *Antimicrob Agents Chemother*, 161: 667-70.
van Belkum et al., 2009. *J Infect Dis.* 199: 1820-26.
Yan et al., 2013. *Cell Host and Microbe*, 14(6): 631-640.

The invention claimed is:

1. A method for treating colonization by *Staphylococcus aureus* in a subject in need thereof, the method comprising administering a pharmaceutical composition comprising (A) at least one *Corynebacterium propinquum* AF1882 (CNCM I-5393) or *Corynebacterium accolens*, (B) *Staphylococcus pasteuri*, and (C) a pharmaceutically acceptable excipient,
   wherein said pharmaceutical composition reduces the colonization of *Staphylococcus aureus* in the subject.

2. The method of claim 1, wherein said composition comprises at least one *Corynebacterium*.

3. The method of claim 1, wherein said composition comprises at least $10^3$ CFUs of *Corynebacterium propinquum* AF1882 (CNCM I-5393) or *Corynebacterium accolens*, and at least $10^3$ CFUs of *Staphylococcus pasteuri*.

4. The method of claim 1, wherein said composition comprises a total of at least $10^3$ bacterial CFUs per dose.

5. The method of claim 4, wherein said composition comprises a total of at least $3\times10^3$ bacterial CFUs per dose.

6. The method of claim 1, wherein said composition further comprises *Staphylococcus epidermidis* strain AF2302 (CNCM I-5394).

7. The method of claim 6, wherein said composition comprises at least $10^3$ CFUs of *S. epidermidis* strain AF2302 (CNCM I-5394) per dose.

8. The method of claim 6, wherein said composition comprises a ratio of *Corynebacterium propinquum* AF1882 (CNCM I-5393) or *Corynebacterium accolens*, to *S. pasteuri* to *S. epidermidis* strain AF2302 (CNCM I-5394) in the range of 1:0.01:0.01 to 1:1:1.

9. The method of claim 1, wherein said pharmaceutically acceptable excipient comprises at least one lyoprotectant.

10. The method of claim 9, wherein said lyoprotectant is selected from the group consisting of peptone, glycerol, lactose, gelatin, glucose, sucrose, trehalose, dextran, maltodextrin, adonitol, and sodium glutamate.

11. The method of claim 1, wherein said composition is lyophilized or freeze-dried, and is reconstituted with at least one pharmaceutically acceptable excipient prior to administration.

12. The method of claim 1, wherein said composition further comprises at least one pharmaceutically acceptable gelling agent.

13. The method of claim 1, wherein said composition is prepared as a patch, gel, cream, lotion, ointment, film, emulsion, or salve.

14. The method of claim 1, comprising administration of the pharmaceutical composition to the anterior nares and/or the skin.

15. The method of claim 1, wherein said *S. aureus* is methicillin-sensitive *Staphylococcus aureus* or methicillin-resistant *Staphylococcus aureus*.

16. The method of claim 1, wherein the subject is colonized by *S. aureus*.

17. The method of claim 1, wherein the subject is at risk of being colonized by *S. aureus*.

18. The method of claim 1, wherein the occurrence of colonization by *S. aureus* in a subject is reduced.

19. The method of claim 1, wherein the patient is not administered antibiotics or antiseptics during the method.

* * * * *